United States Patent
Jung et al.

(10) Patent No.: US 9,624,310 B2
(45) Date of Patent: Apr. 18, 2017

(54) METHODS OF USING BI-SPECIFIC ANTIBODIES FOR TREATING B-CELL-MEDIATED AUTOIMMUNE DISEASES OR AUTO-REACTIVE B-CELLS

(71) Applicant: Gundram Jung, Rottenburg-Wendelsheim (DE)

(72) Inventors: Gundram Jung, Rottenburg-Wendelsheim (DE); Ludger Grosse-Hovest, Tübingen (DE)

(73) Assignee: Jung Gundram, Rottenburg-Wendelsheim (DE)

( * ) Notice: Subject to any disclaimer, the term of this patent is extended or adjusted under 35 U.S.C. 154(b) by 0 days.

(21) Appl. No.: 14/358,797

(22) PCT Filed: Nov. 19, 2012

(86) PCT No.: PCT/EP2012/072986
§ 371 (c)(1),
(2) Date: May 16, 2014

(87) PCT Pub. No.: WO2013/072523
PCT Pub. Date: May 23, 2013

(65) Prior Publication Data
US 2014/0314764 A1    Oct. 23, 2014

Related U.S. Application Data

(60) Provisional application No. 61/560,867, filed on Nov. 17, 2011.

(51) Int. Cl.
C07K 16/46     (2006.01)
C07K 16/28     (2006.01)
A61K 39/395    (2006.01)

(52) U.S. Cl.
CPC ........ *C07K 16/468* (2013.01); *A61K 39/3955* (2013.01); *C07K 16/2878* (2013.01); *C07K 16/2887* (2013.01); *C07K 2317/31* (2013.01); *C07K 2317/524* (2013.01); *C07K 2317/53* (2013.01); *C07K 2317/54* (2013.01); *C07K 2317/55* (2013.01); *C07K 2317/622* (2013.01); *C07K 2317/64* (2013.01); *C07K 2317/73* (2013.01); *C07K 2319/00* (2013.01)

(58) Field of Classification Search
CPC .................................................. A61K 39/3955
See application file for complete search history.

(56) References Cited

U.S. PATENT DOCUMENTS 8,058,399 B2 * 11/2011 Jung .......................... 530/387.1
2003/0232049 A1    12/2003 Jung

FOREIGN PATENT DOCUMENTS

| WO | 02/08291 A2 | 1/2002 |
|---|---|---|
| WO | 0228904 A2 | 4/2002 |
| WO | 02066516 A2 | 8/2002 |
| WO | 2004056312 A2 | 7/2004 |
| WO | 2005044306 | 5/2005 |
| WO | 2011047180 A1 | 4/2011 |
| WO | 2014076292 A1 | 5/2014 |

OTHER PUBLICATIONS

Paul, WE. Fundamental Immunology, 3rd ed. Raven Press, NY, Chap. 9, pp. 292-295, 1993.*
Rudikoff S. et al. Proc. Natl. Acad. Sci. USA, 79:1979-1983, 1982.*
Colman, PM. Research in Immunology, Elsevier, NY, 145(1):33-36, 1994.*
Lens et al. J. Immunol., 156(2):507-14, 1996.*
An, Z., et al., mAbs, 1(6):572-579 , Nov./Dec. 2009. Available online at—www.landesbioscience.com/journals/mabs/article/10185.*
Edwards JC, et al. Rheumatology (Oxford) 40(2):205-11. 2001. Available online at—doi: 10.1093/rheumatology/40.2.205.*
Huck S, et al. J. Autoimmunity. 11:449-455, 1998. Available online at—doi:10.1006/jaut.1998.0226.*
Cohen SB et al.Arthritis Rheum. 54(9):2793-806. 2006. Available online at—doi: 10.1002/art.22025.*
Emery P, et al. Arthritis Rheum. 54(5):1390-400. 2006. Available online at—doi: 10.1002/art.21778.*
Ricci-Vitiani L, et al. Apoptosis 5:419-424, 2000.*
Jung, G. et al. (2001). Target cell-restricted triggering of the CD95 (APO-1/Fas) death receptor with bispecific antibody fragments. Cancer research, 61(5), 1846-1848.
Otz, T. et al. (2011). Target Cell-Restricted Stimulation of the CD95 (APO-1/Fas) death receptor with various bispecific CD20XCD95 antibodies. Advances in Experimental Medicine and Biology, 691, 797-798.
Hermann, T. et al. (2008). Construction of optimized bispecific antibodies for selective activation of the death receptor CD95. Cancer research, 68(4), 1221-1227.
Wischhusen, J. et al. (2005). Death receptor-mediated apoptosis in human malignant glioma cells: modulation by the CD40/CD40L system. Journal of neuroimmunology, 162(1), 28-42.
Silverman, G. J. (2007). Anti-CD20 therapy and autoimmune disease: therapeutic opportunities and evolving insights. Frontiers in bioscience: a journal and virtual library, 12, 2194-2206.
Ping, L. et al. (2005). Novel role of CD40 in Fas—dependent apoptosis of cultured salivary epithelial cells from patients with Sjogren's syndrome. Arthritis & Rheumatism, 52(2), 573-581.
Yonehara, S. (2002). Death receptor Fas and autoimmune disease: from the original generation to therapeutic application of agonistic anti-Fas monoclonal antibody. Cytokine & growth factor reviews, 13(4), 393-402.
Wang, J. et al. (2004). The role of pathogenic B-cell clones in antibody mediated autoimmune disorders. Journal of Dermatological Science, 36(3), 141-148.

(Continued)

*Primary Examiner* — Robert Landsman
(74) *Attorney, Agent, or Firm* — Meunier Carlin & Curfman LLC

(57) ABSTRACT

A bispecific antibody format devoid of an active Fc moiety comprising a monovalent binding site for a death receptor and at least one binding site for a cell surface antigen expressed on B-cells, for use in the treatment or prevention of B cell mediated autoimmune diseases.

30 Claims, 14 Drawing Sheets

(56) References Cited

OTHER PUBLICATIONS

Figure 1A:
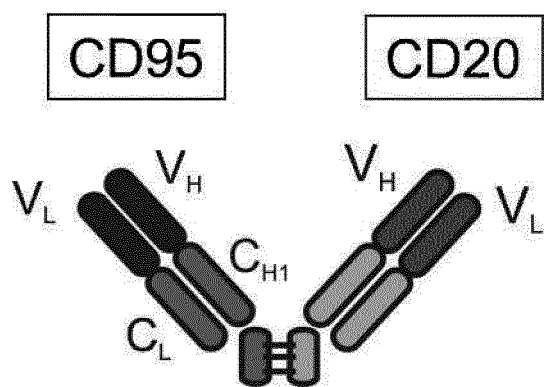

Nalivaiko, K. et al. (2011). Inhibition of antibody production in vitro with bispecific CD20 X CD95 antibodies. In Blood (vol. 118, No. 21, pp. 510-510). 1900 M Street. Nw Suite 200, Washington, DC 20036 USA: Amer Soc Hematology.

Jung et al. (1991). Target cell-induced T cell activation with bi- and trispecific antibody fragments. Eur J Immunol, 21, 2431-2435.

Liu A. et al. (1987). Production of a mouse-human chimeric monoclonal antibody to DC20 with potent Fc-dependent biologic activity. Journal of Immunology, 139, 3521-3526.

International Search Report, Received in related application PCT/EP2012/072986, Mailed Apr. 17, 2013.

Written Opinion of the International Searching Authority, Received in related application PCT/EP2012/072986, Mailed May 30, 2014.

Clark et al. "How does B cell depletion therapy work, and how can it be improved?" Ann Rheum Dis 2005 64: iv77-iv80.

International Preliminary Report on Patentability and Written Opinion dated May 19, 2015 from corresponding application No. PCT/EP2013/074142 filed Nov. 19, 2013, 9 pages.

International Search Report and Written Opinion dated Dec. 16, 2013 from corresponding application No. PCT/EP2013/074142 filed Nov. 19, 2013, 14 pages.

Shijing et al., Clinical Immunological Assay, Chinese Medical Science and Technology Press, pp. 371, 200408; accessed Aug. 25, 2016; English Translation.

Zhiwei et al., Antibody Engineering, Peking Medical University & Peking Union Medical College Associated Press: pp. 255, 200206; accessed Aug. 25, 2016; English Translation.

Bosma, et al., "A severe combined immunodeficiency mutation in the mouse", Nature, 1983, 527-530.

Lifely, et al., "Glycosylation and biological activity of CAMPATH-1H expressed in differernt cell lines and grown under different culture conditions", Glycobiology 5, 1995, 813-822.

Tobon, et al., "B cell-targeted therapies in Sjogren's syndrome", Autoimmunity Reviews 9, 2010, 224-228.

* cited by examiner

Fig. 9A: murine sequences of an anti-CD95 antibody (Apo-1)

>APO-VL
mouse kappa subgroup III

SEQ ID 1:
DIVLTQSPASLAVSLGQRATISCRASESVEYYGTSLMQWYQQKPGQPPKLLIYVASNVES
GVPARFSGSGSGTDFSLNIHPVEEDDIAMYFCQQSTKVPWTFGGGTKLEIKR

CDR-L1: RASESVEYYGTSLMQ (SEQ ID 2)
CDR-L2: VASNVES (SEQ ID 3)
CDR-L3: QQSTKVPWT (SEQ ID 4)

>APO-VH
mouse heavy subgroup IIId

SEQ ID 5:
EVQLVETGGGLVQPKGSLKLSCAASGFTFNTNAMNWVRQAPGKGLEWVARIRSKSNNYAT
YYAESVKDRFTISRDDSQSMLYLQMNNLKAEDTAMYYCVTDGYYWGQGTTLTVSS

CDR-H1: TNAMN (SEQ ID 6)
CDR-H2: RIRSKSNNYATYYAESVKD (SEQ ID 7)
CDR-H3: DGYY (SEQ ID 8)

Fig. 9B: humanised sequences of an anti-CD95 antibody (Apo-1)

>humApo-VL
human kappa subgroup IV

SEQ ID 9:
DIVMTQSPDSLAVSLGERATISCRASESVEYYGTSLMQWYQQKPGQPPKLLIYVASNVES
GVPDRFSGSGSGTDFTLTISSLQAEDVAVYFCQQSTKVPWTFGQGTKLEIK

>humApo-VH
human subgroup III

SEQ ID 10:
EVQLVESGGGLVKPGGSLRLSCAASGFTFNTNAMNWVRQAPGKGLEWVARIRSKSNNYAT
YYAESVKDRFTISRDDSKNTLYLQMNSLKTEDTAVYYCVTDGYYWGQGTTLTVSS

Fig. 9C: murine sequences anti-CD20 antibody

>CD20-VL (accession # M17953)
mouse kappa subgroup VI

SEQ ID 11:
DIVLSQSPAILSASPGEKVTMTCRASSSVSYMHWYQQKPGSSPKPWIYAPSNLASGVPARFS
GSGSGTSYSLTISRVEAEDAATYYCQQWSFNPPTFGAGTKLELK

CDR-L1: RASSSVSYM (SEQ ID 12)
CDR-L2: APSNLAS (SEQ ID 13)
CDR-L3: QQWSFNPPT (SEQ ID 14)

>CD20-VH (accession # M17954)
mouse heavy subgroup IIb

SEQ ID 15:
QAYLQQSGAELVRPGASVKMSCKASGYTFTSYNMHWVKQTPRQGLEWIGAIYPGNGDTSYNQK
FKGKATLTVDKSSSTAYMQLSSLTSEDSAVYFCARVVYYSNSYWYFDVWGTGTTVTVSS

CDR-H1: SYNMH (SEQ ID 16)
CDR-H2: AIYPGNGDTSYNQKFKG (SEQ ID 17)
CDR-H3: VVYYSNSYWYFDV (SEQ ID 18)

Fig. 9D: humanised sequences anti-CD20 antibody

>humCD20-VL
human kappa subgroup I

SEQ ID 19:
DIQMTQSPSSLSASVGDRVTITCRASSSVSYMHWYQQKPGKAPKPLIYAPSNLASGVPSRFS
GSGSGTDFTLTISSLQPEDFATYYCQQWSFNPPTFGQGTKLEIK

>humCD20-VH
human subgroup I

SEQ ID 20:
QVQLVQSGAEVKKPGASVKVSCKASGYTFTSYNMHWVRQAPGQGLEWIGAIYPGNGDTSYNQK
FKGRVTITRDTSASTAYMELSSLRSEDTAVYYCARVVYYSNSYWYFDVWGQGTLVTVSS

Fig. 9E: Bispecific antibody CD95xCD20 (bsFabXsc-format, depicted in Fig.1B)

i) chimeric versions light-chain (chimeric version):

CD95-VJ + human CL (kappa); chimeric light chain w/o leader peptide

SEQ ID 21:
```
  1    DIVLTQSPAS LAVSLGQRAT ISCRASESVE YYGTSLMQWY QQKPGQPPKL
 51    LIYVASNVES GVPARFSGSG SGTDFSLNIH PVEEDDIAMY FCQQSTKVPW
101    TFGGGTKLEI KRTVAAPSVF IFPPSDEQLK SGTASVVCLL NNFYPREAKV
151    QWKVDNALQS GNSQESVTEQ DSKDSTYSLS STLTLSKADY EKHKVYACEV
201    THQGLSSPVT KSFNRGEC*
```

Amino acid 1-111: anti-CD95 VJ (mouse)
underlined: human constant kappa chain heavy-chain (chimeric version):

CD95-VDJ + human CH1 + hinge + modified CH2 + CD20scFv (VH-VL)

chimeric heavy chain w/o leader-peptide

SEQ ID 22:
```
  1    EVQLVETGGG LVQPKGSLKL SCAASGFTFN TNAMNWVRQA PGKGLEWVAR
 51    IRSKSNNYAT YYAESVKDRF TISRDDSQSM LYLQMNNLKA EDTAMYYCVT
101    DGYYWGQGTT LTVSSASTKG PSVFPLAPSS KSTSGGTAAL GCLVKDYFPE
151    PVTVSWNSGA LTSGVHTFPA VLQSSGLYSL SSVVTVPSSS LGTQTYICNV
201    NHKPSNTKVD KKVEPKSCDK THTSPPSPAP PVAGPSVFLF PPKPKDTLMI
251    SRTPEVTCVV VGVSHEDPEV KFNWYVDGVE VHNAKTKPRE EQYQSTYRVV
301    SVLTVLHQDW LNGKEYKCKV SNKQLPSPIE KTISKAKGQP SGQAYLQQSG
351    AELVRPGASV KMSCKASGYT FTSYNMHWVK QTPRQGLEWI GAIYPGNGDT
401    SYNQKFKGKA TLTVDKSSST AYMQLSSLTS EDSAVYFCAR VVYYSNSYWY
451    FDVWGTGTTV TVSSGGGGSG GGGSGGGGSD IVLSQSPAIL SASPGEKVTM
501    TCRASSSVSY MHWYQQKPGS SPKPWIYAPS NLASGVPARF SGSGSGTSYS
551    LTISRVEAED AATYYCQQWS FNPPTFGAGT KLELK**
```

- Amino acids 1-115: anti-CD95 VDJ (mouse)
- amino acids underlined: human CH1, modified hinge and modified CH2 followed by GQP (= first three amino acids from CH3) followed by amino acids SG
- *italic* amino acids 343 – 464 anti-CD20 (VH) GenBank # M17953
- GGGGSGGGGSGGGGS (SEQ ID 23) linker element between Vh and Vl
- bold amino acids 480 – end (585) anti-CD20 (VL) GenBank # M17954

Fig. 9E (continued)

ii) humanised versions humanised CD95-VJ + human CL

SEQ ID 24:

```
        DIVMTQSPDSLAVSLGERATISCRASESVEYYGTSLMQWYQQKPGQPPKLLIYVASNVES
    1   ---------+---------+---------+---------+---------+---------+   60
        GVPDRFSGSGSGTDFTLTISSLQAEDVAVYFCQQSTKVPWTFGQGTKLEIKRTVAAPSVF
   61   ---------+---------+---------+---------+---------+---------+  120
        IFPPSDEQLKSGTASVVCLLNNFYPREAKVQWKVDNALQSGNSQESVTEQDSKDSTYSLS
  121   ---------+---------+---------+---------+---------+---------+  180
        STLTLSKADYEKHKVYACEVTHQGLSSPVTKSFNRGEC*
  181   ---------+---------+---------+---------  219
``` humanised CD95-VDJ-CH1-H-CH2(attenuated)- humanised CD20scFv (VH-VL)

SEQ ID 25:

```
        EVQLVESGGGLVKPGGSLRLSCAASGFTFNTNAMNWVRQAPGKGLEWVARIRSKSNNYAT
    1   ---------+---------+---------+---------+---------+---------+   60
        YYAESVKDRFTISRDDSKNTLYLQMNSLKTEDTAVYYCVTDGYYWGQGTTLTVSSASTKG
   61   ---------+---------+---------+---------+---------+---------+  120
        PSVFPLAPSSKSTSGGTAALGCLVKDYFPEPVTVSWNSGALTSGVHTFPAVLQSSGLYSL
  121   ---------+---------+---------+---------+---------+---------+  180
        SSVVTVPSSSLGTQTYICNVNHKPSNTKVDKKVEPKSCDKTHTSPPSPAPPVAGPSVFLF
  181   ---------+---------+---------+---------+---------+---------+  240
        PPKPKDTLMISRTPEVTCVVVCVSHEDPEVKFNWYVDGVEVHNAKTKPREEQYQSTYRVV
  241   ---------+---------+---------+---------+---------+---------+  300
        SVLTVLHQDWLNGKEYKCKVSNKQLPSPIEKTISKAKGQPSGQVQLVQSGAEVKKPGASV
  301   ---------+---------+---------+---------+---------+---------+  360
        KVSCKASGYTFTSYNMHWVRQAPGQGLEWIGAIYPGNGDTSYNQKFKGRVTITRDTSAST
  361   ---------+---------+---------+---------+---------+---------+  420
        AYMELSSLRSEDTAVYYCARVVYYSNSYWYFDVWGQGTLVTVSSGGGGSGGGGSGGGGSD
  421   ---------+---------+---------+---------+---------+---------+  480
        IQMTQSPSSLSASVGDRVTITCRASSSVSYMHWYQQKPGKAPKPLIYAPSNLASGVPSRF
  481   ---------+---------+---------+---------+---------+---------+  540
        SGSGSGTDFTLTISSLQPEDFATYYCQQWSFNPPTFGQGTKLEIK**
  541   ---------+---------+---------+-------  587
```

METHODS OF USING BI-SPECIFIC ANTIBODIES FOR TREATING B-CELL-MEDIATED AUTOIMMUNE DISEASES OR AUTO-REACTIVE B-CELLS

The invention refers to a new medical use of a bispecific antibody having no or impaired Fc moiety and having a monovalent binding site for a death receptor and at least one binding site for a cell surface antigen expressed on B cells, for B cell dependent autoimmune disease

BACKGROUND

CD95/Fas/Apo-1 is a cell surface receptor capable of inducing apoptotic death of human cells. Similar to the physiologic ligand of this receptor, CD95L, agonistic anti-CD95 antibodies may induce apoptosis if binding to CD95 occurs in a multimeric format, e.g., as pentameric IgM or self-aggregating IgG3. Alternatively, anti-CD95 antibodies may be cross-linked by Fc receptors on neighboring cells or by secondary antibodies to achieve agonistic activity.

Because many tumor cells express CD95, the use of agonistic anti-CD95 antibodies for tumor therapy has been vigorously pursued after initial characterization of prototypic CD95 antibodies. However, it soon became obvious that, at least in its most simple form of applying agonistic anti-CD95 antibodies or recombinant CD95L to patients, this approach fails because many normal cell types express functional CD95 and may be killed by agonistic antibodies.

CD20 is a marker of B-cells involved in many lymphoma and autoimmune diseases, e.g. multiple sclerosis (MS), rheumatoid arthritis (RA) and systemic lupus erythematosus (SLE).

Antibodies directed against the B-cell associated CD20 surface antigen can target normal as well as malignant B cells. They are successfully used for the treatment of B-cell derived leukaemia and lymphoma and antibody mediated autoimmune disease, respectively. Rituximab (trade names Rituxan and MabThera) is a chimeric monoclonal antibody against the protein CD20. Rituximab destroys B cells, and is therefore used to treat diseases which are characterized by excessive numbers of B cells, overactive B cells, or dysfunctional B cells. This includes many lymphomas, leukaemias, transplant rejection, and some autoimmune disorders.

However, rituximab kills CD20-positive cells non-specifically, and was shown to be clinically effective in MS but is compromised by side effects (e.g. Progressive Multifocal Leukoencephalopathy, PML).

It was previously shown that bispecific F(ab')$_2$ fragments (bs-F(ab')$_2$) with specificity for CD95 and different target antigens on lymphoma cells, such as CD20 and CD40, induce the apoptosis of cells positive for CD95 and the respective target antigen. Lymphoma cells expressing CD95 but no target antigen were not killed (Jung et al. Cancer Research 61, 1846-1848 (2001)).

Herrmann et al. (Cancer Research 68 (4): 1221-7 (2008) assessed the influence of the antibody format and nature of the target antigen on selective CD95 mediated apoptosis in tumor cells.

US2003/0232049A1 describes a multispecific reagent for selectively stimulating cell surface receptors. Bi-specific antibodies consisting of antigen-binding antibody fragments with a first binding site for a cell surface receptor, such as a death receptor, e.g. CD95, and a second binding site for a target antigen of the same cell, such as CD20 or CD40, are described to kill cancer cells.

SUMMARY OF THE INVENTION

It is the objective of the invention to provide for a selective immunotherapy of B-cell related disease or disorder, in particular autoimmune disease.

The object is solved by the subject matter as claimed.

According to the invention there is provided a bispecific antibody format devoid of an active Fc moiety comprising a monovalent binding site for a death receptor and at least one binding site for a cell surface antigen expressed on B-cells, for use in the treatment or prevention of an auto-reactive B-cell disorder.

Figure 1B:
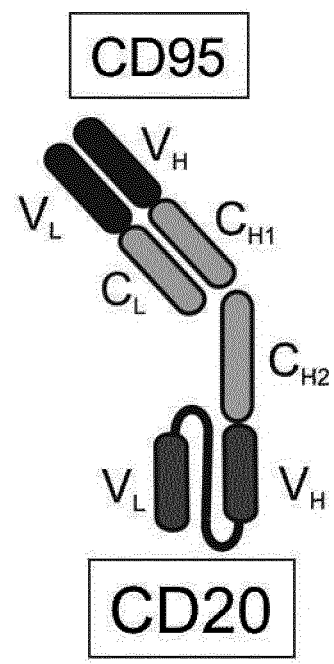

Specifically, the antibody format comprises a structure as depicted in FIG. 1A or FIG. 1B.

Specifically the death receptor is selected from the group consisting of CD95, the TRAIL receptors and the TNF receptors, preferably CD95.

Specifically, the cell surface antigen is selected from the group consisting of CD19, CD20 and CD40, preferably CD20.

According to a specific embodiment, the format comprises a monovalent binding site specifically binding CD95 and at least one binding site specifically binding CD19, CD20 or CD40.

According to a specific aspect, the bispecific antibody format is provided for use according to the invention, wherein the auto-reactive B-cell disorder is caused by an aberrant, excessive or undesired immune response. Specifically the disease to be treated is caused by normal, activated rather than malignant B cells.

The invention is specifically related to combatting auto-reactive B-cells and the treatment or prevention of disease conditions related thereto. B-cell derived leukemia and lymphoma, like any other cancer, is associated with excessive B-cell production and related disease conditions irrespective of the specificity or reactivity of the B-cells. Therefore, prevention and treatment of such leukemia, lymphoma or cancer is specifically excluded from the disease treatment according to the invention.

Specifically, the auto-reactive B-cell disorder is an autoimmune disorder, preferably selected from the group consisting of systemic lupus erythematosus, Sjögren's syndrome, scleroderma, rheumatoid arthritis, juvenile idiopathic arthritis, graft versus host disease, dermatomyositis, type I diabetes mellitus, Hashimoto's thyroiditis, Graves's disease, Addison's disease, celiac disease, Crohn's Disease, pernicious anaemia, Pemphigus vulgaris, Vitiligo, autoimmune haemolytic anaemia, idiopathic thrombocytopenic purpura, giant cell arteritis, Myasthenia gravis, multiple sclerosis (MS), preferably relapsing-remitting MS (RRMS), glomerulonephritis, Goodpasture's syndrome, bullous pemphigoid, colitis ulcerosa, Guillain-Barré syndrome, chronic inflammatory demyelinating polyneuropathy, Anti-phospholipid syndrome, narcolepsy, sarcoidosis, and Wegener's granulomatosis.

According to a specific aspect of the invention, the bispecific antibody format is a recombinant molecule comprising at least 2 antibody domains, preferably at least 3, 4, 5, 6, 7 or 8 antibody domains, and optionally a hinge region. A preferred recombinant bispecific antibody format is depicted in FIG. 1B. Antibodies or antibody fragments may comprise or consist of such antibody domains and hinge region, preferably monoclonal antibodies, monoclonal antibody fragments or other monoclonal antibody formats, either comprising the native amino acid sequence or comprising one or more mutations of the amino acid sequence, the tertiary structure and optionally the glycosylation, e.g. to improve the specificity, the affinity and/or avidity of binding to a target, or to improve the stability of the format, or to increase the producability of the recombinant molecule.

Specifically, the antibody domains are of mammalian origin, such as rodent, e.g. murine, or human origin, or chimeric or humanized antibody domains of mammalian origin other than human, such as humanized murine or camelid antibody domains.

The bispecific antibody format specifically comprises at least 2 binding sites formed by complementary determining regions (CDR), preferably CDRs derived from antibody domains selected from the group consisting of VH and VH/VL domain pairs, preferably at least one or two VH domains and/or at least one or two VH/VL domain pairs. Specifically, bispecific antibody formats are obtained by chemical hybridization of two Fab-fragments with different specificity as described in Jung et al. Eur J Immunol 21:2431, 1991. Bispecific antibody formats may also be obtained by the hybrid-hybridoma technique or by recombinant antibody technology.

Specifically, the format comprises at least one of a VH/VL binding site and/or scFv binding site, and optionally at least one of an antibody constant domain, specifically a CH1, CL, CH2 or CH3 domain.

According to a preferred embodiment the format comprises at least one VH/VL antibody domain pair and at least one scFv binding site, optionally with any of the constant domains, specifically including CH2, CH1 and CL domains, which are preferably used as a linker between the variable domains that incorporate the specific binding sites.

According to another preferred embodiment, the format comprises at least two single VH antibody domains, preferably single VHH domains.

Specifically, the format is selected from the group consisting of scFv, a combination of a Fab or F(ab') fragment with one or more antibody variable domains, F(ab')$_2$, and combinations thereof, preferably employing at least one antibody constant domain as a linker.

According to a specific embodiment, the format is a construct comprising or consisting of a) a Fab fragment consisting of a VL/VH domain pair and a CL/CH1 domain pair, which Fab fragment comprises the first binding site;

b) an scFv consisting of VH/VL domains linked to each other; and c) a CH2 domain linking the CH1 domain of the Fab fragment of a) to the VH domain of the scFv of b).

According to a further specific embodiment, there is provided a bispecific antibody format for use according to the invention, which comprises or consists of a Fab fragment comprising a first binding site for a first antigen;

an scFv fragment comprising a second binding site for a second antigen; and a CH2 domain, wherein the Fab fragment and the scFv fragment are linked via the CH2 domain, wherein a) the first antigen is CD95 and the second antigen is selected from CD19, CD20 and CD40, preferably CD20; or b) the first antigen is selected from CD19, CD20 and CD40, preferably CD20, and the second antigen is CD95.

Specifically the binding site that binds CD20 comprises six complementarity determining regions of antibody variable domains (CDR1 to CDR6), wherein

A)

i) CDR1 comprises the amino acid sequence RASSSV-SYM (SEQ ID 12);

ii) CDR2 comprises the amino acid sequence APSNLAS (SEQ ID 13);

iii) CDR3 comprises the amino acid sequence QQWSF-NPPT (SEQ ID 14);

iv) CDR4 comprises the amino acid sequence SYNMH (SEQ ID 16);

v) CDR5 comprises the amino acid sequence AIYPGNGDTSYNQKFKG (SEQ ID 17); and vi) CDR6 comprises the amino acid sequence VVYYSN-SYWYFDV (SEQ ID 18);

or

B) a functionally active variant thereof, wherein at least one of i) CDR1 comprises an amino acid sequence that has at least 70% sequence identity with the amino acid sequence RASSSVSYM (SEQ ID 12), or at least 80% or at least 90%;

ii) CDR2 comprises an amino acid sequence that has at least 70% sequence identity with the amino acid sequence APSNLAS (SEQ ID 13), or at least 80% or at least 90%;

iii) CDR3 comprises an amino acid sequence that has at least 70% sequence identity with the amino acid sequence QQWSFNPPT (SEQ ID 14), or at least 80% or at least 90%;

iv) CDR4 comprises an amino acid sequence that has at least 70% sequence identity with the amino acid sequence SYNMH (SEQ ID 16), or at least 80% or at least 90%;

v) CDR5 comprises an amino acid sequence that has at least 70% sequence identity with the amino acid sequence AIYPGNGDTSYNQKFKG (SEQ ID 17), or at least 80% or at least 90%; and/or vi) CDR6 comprises an amino acid sequence that has at least 70% sequence identity with the amino acid sequence WYYSNSYWYFDV (SEQ ID 18), or at least 80% or at least 90%.

The invention specifically contemplates the use of any antibody format comprising an CD20 binding site derived from the sequences A i) to vi) above, e.g. the CDR1, CDR2 and CDR3 sequences of the light chain variable region and/or the CDR4, CDR5 and CDR6 sequences of the heavy chain variable region, including constructs comprising single variable domains comprising either of the combination of the CDR1, CDR2 and CDR3 sequences, or the combination of the CDR4, CDR5 and CDR6 sequences, or pairs of such single variable domains, e.g. VH, VHH or VH/VL domain pairs.

Specific embodiments refer to the antibody format comprising at least one of the CDR sequences of A, preferably at least two or at least three, and at least one of the CDR sequences of B.

Further specific embodiments refer to the antibody format comprising at least one of the CDR sequences of B, preferably at least two or at least three, and at least one of the CDR sequences of A.

Specific embodiments refer to the use of a light chain variable region comprising the CDR1 sequence of A i), the CDR2 of sequence of A ii) and the CDR3 sequence of A iii), and a heavy chain variable region comprising the CDR4 sequence of A iv) or B iv), the CDR5 sequence of A v) or B v) and the CDR6 sequence of A vi) or B vi), wherein at least one of the CDR4, CDR5 and CDR6 sequences comprises a functionally active variant of B.

Further specific embodiments refer to the use of a heavy chain variable region comprising the CDR4 sequence of A iv), the CDR5 of sequence of A v) and the CDR6 sequence of A vi), and a light chain variable region comprising the CDR1 sequence of A i) or B i), the CDR2 sequence of A ii) or B ii) and the CDR3 sequence of A iii) or B iii), wherein at least one of the CDR1, CDR2 and CDR3 sequences comprises a functionally active variant of B.

A variant of B optionally comprise the specific CDR sequence as listed, which contains one, two or three point mutations, e.g. by insertion, deletion, substitution or chemical derivatization of an amino acid residue.

Variants of a CD20 binder are considered functionally active variants, if binding to CD20, specifically human CD20, in particular with a high affinity, e.g. with a Kd< $10^{-8}$M.

Further functionally active variants have functional activity targeting activated B-cells, e.g. the apoptotic activity, as determined in a test as described in the examples.

According to a specific embodiment, the antibody format comprises a VL domain comprising or consisting of the amino acid sequence of SEQ ID 11 and/or a VH domain comprising of consisting of the amino acid sequence of SEQ ID 15, or functionally active variants thereof.

Specifically, the variant is a humanized variant comprising a VL domain comprising or consisting of the amino acid sequence of SEQ ID 19 and/or a VH domain comprising or consisting of the amino acid sequence of SEQ ID 20, or a functionally active variant thereof.

Specifically the binding site that binds CD95 comprises six complementarity determining regions of variable antibody domains (CDR1 to CDR6), wherein A)
i) CDR1 comprises the amino acid sequence RASESVEYYGTSLMQ (SEQ ID 2);
ii) CDR2 comprises the amino acid sequence VASNVES (SEQ ID 3);
iii) CDR3 comprises the amino acid sequence QQSTKVPWT (SEQ ID 4);
iv) CDR4 comprises the amino acid sequence TNAMN (SEQ ID 6);
v) CDR5 comprises the amino acid sequence RIRSKSNNYATYYAESVKD (SEQ ID 7); and
vi) CDR6 comprises the amino acid sequence DGYY (SEQ ID 8);
or
B) a functionally active variant thereof, wherein at least one of
i) CDR1 comprises an amino acid sequence that has at least 70% sequence identity with the amino acid sequence RASESVEYYGTSLMQ (SEQ ID 2), or at least 80% or at least 90%;
ii) CDR2 comprises an amino acid sequence that has at least 70% sequence identity with the amino acid sequence VASNVES (SEQ ID 3), or at least 80% or at least 90%;
iii) CDR3 comprises an amino acid sequence that has at least 70% sequence identity with the amino acid sequence QQSTKVPWT (SEQ ID 4), or at least 80% or at least 90%;
iv) CDR4 comprises an amino acid sequence that has at least 70% sequence identity with the amino acid sequence TNAMN (SEQ ID 6), or at least 80% or at least 90%;
v) CDR5 comprises an amino acid sequence that has at least 70% sequence identity with the amino acid sequence RIRSKSNNYATYYAESVKD (SEQ ID 7), or at least 80% or at least 90%; and/or
vi) CDR6 comprises an amino acid sequence that has at least 70% sequence identity with the amino acid sequence DGYY (SEQ ID 8), or at least 80% or at least 90%.

The invention specifically contemplates the use of any antibody format comprising an CD95 binding site derived from the sequences A i) to vi) above, e.g. the CDR1, CDR2 and CDR3 sequences of the light chain variable region and/or the CDR4, CDR5 and CDR6 sequences of the heavy chain variable region, including constructs comprising single variable domains comprising either of the combination of the CDR1, CDR2 and CDR3 sequences, or the combination of the CDR4, CDR5 and CDR6 sequences, or pairs of such single variable domains, e.g. VH, VHH or VH/VL domain pairs.

Specific embodiments refer to the antibody format comprising at least one of the CDR sequences of A, preferably at least two or at least three, and at least one of the CDR sequences of B.

Further specific embodiments refer to the antibody format comprising at least one of the CDR sequences of B, preferably at least two or at least three, and at least one of the CDR sequences of A.

Specific embodiments refer to the use of a light chain variable region comprising the CDR1 sequence of A i), the CDR2 of sequence of A ii) and the CDR3 sequence of A iii), and a heavy chain variable region comprising the CDR4 sequence of A iv) or B iv), the CDR5 sequence of A v) or B v) and the CDR6 sequence of A vi) or B vi), wherein at least one of the CDR4, CDR5 and CDR6 sequences comprises a functionally active variant of B.

Further specific embodiments refer to the use of a heavy chain variable region comprising the CDR4 sequence of A iv), the CDR5 of sequence of A v) and the CDR6 sequence of A vi), and a light chain variable region comprising the CDR1 sequence of A i) or B i), the CDR2 sequence of A ii) or B ii) and the CDR3 sequence of A iii) or B iii), wherein at least one of the CDR1, CDR2 and CDR3 sequences comprises a functionally active variant of B.

A variant of B optionally comprise the specific CDR sequence as listed, which contains one, two or three point mutations, e.g. by insertion, deletion, substitution or chemical derivatization of an amino acid residue.

Variants of a CD95 binder are considered functionally active variants, if binding to CD95, specifically human CD95, in particular with a high affinity, e.g. with a Kd<$10^{-8}$M.

Further functionally active variants have functional activity targeting activated B-cells, e.g. the apoptotic activity, as determined in a test as described in the examples.

According to a specific embodiment, the antibody format comprises a VL domain comprising or consisting of the amino acid sequence of SEQ ID 1 and/or a VH domain comprising or consisting of the amino acid sequence of SEQ ID 5, or functionally active variants thereof.

Specifically the variant is a humanized variant comprising a VL domain comprising or consisting of the amino acid sequence of SEQ ID 9 and/or a VH domain comprising or consisting of the amino acid sequence of SEQ ID 10, or a functionally active variant thereof.

According to a specific embodiment, the antibody format comprises or consists of a light chain sequence of SEQ ID 21 and a heavy chain sequence of SEQ ID 22, or functionally active variants thereof.

Specifically the variant is a humanized variant comprising a VL domain comprising or consisting of the amino acid sequence of SEQ ID 24 and/or a VH domain comprising or consisting of the amino acid sequence of SEQ ID 25, or a functionally active variant thereof.

The bispecific antibody format according to the invention specifically comprises murine, chimeric, humanized and/or human sequences.

Preferably the bispecific antibody format binds an antigen selected from CD19, CD20 and CD40, preferably CD20, with a Kd<$10^{-8}$ M and/or binds CD95 with a Kd<$10^{-8}$ M.

An exemplary construct is a recombinant bispecific Fab-single chain (bsFabXsc) with CD20×CD95-specificity schematically described in FIG. 1B. It is termed NA-C20.

Specifically, the format is lacking an Fc moiety or comprises an Fc moiety engineered to inactivate or reduce its Fc effector function, preferably by one or more mutations in the Fc moiety. Exemplary mutations for reduced Fc effector function are in the Fcgamma receptor binding region of the antibody Fc fragment, preferably in the N-terminal CH2 region. Mutations by molecular engineering and/or chemical engineering are feasible. Preferred mutations are point mutations in the amino acid sequence, e.g. insertions and/or deletions and/or substitutions. Further preferred mutations are by chemical derivatization of amino acids.

Inactivated or reduced Fc effector function may be determined by a suitable assay for determining ADCC and/or CDC activity of the antibody format. Results are compared to the activity of the corresponding wild-type molecule.

Specifically, the format may be derived from an antibody of the IgG class, in particular, any of the IgG1, IgG2 or IgG4 subclasses, specifically comprising sequences derived from a human IgG antibody.

Specifically the format may be derived from a human IgG antibody.

According to a specific embodiment, the bispecific antibody format is provided for use according to the invention in a combination therapy with other treatment of an auto-reactive B-cell disorder, preferably a combination with cytokine treatment, such as interferon, in particular interferon-beta, or treatment with other antibody formats or agents.

Specifically, the bispecific antibody format for use according to the invention is administered to a subject in need thereof in a therapeutically effective amount, preferably provided in a formulation for parenteral use, e.g. intravenous or subcutaneous formulation, in particular in a pharmaceutical preparation which comprises the antibody format and optionally a pharmaceutically acceptable carrier or excipient.

According to a specific aspect, the invention provides for a method for the treatment or prevention of an auto-reactive B-cell disorder comprising administering a therapeutically effective amount of bispecific antibody format devoid of an active Fc moiety comprising a monovalent binding site for a death receptor and at least one binding site for a cell surface antigen expressed on B-cells to a subject in need thereof.

Specifically, such method for the treatment or prevention of an auto-reactive B-cell disorder is characterized by the embodiments related to the medical use as described herein.

According to another aspect of the invention, a method is provided for treating auto-reactive B-cells, comprising contacting said cells with a composition comprising the bispecific antibody format of the invention. Such treatment method may be in vivo or ex vivo.

Specifically, a death receptor and a cell surface antigen being expressed by said cells are targeted by the bispecific antibody format, whereby the IgG production by said cells is inhibited, and optionally apoptosis of said cells is achieved.

FIGURES

FIGS. 1A-1B: Schematic description of two exemplary antibody formats: Two different formats of bispecific CD20×CD95 antibodies for the selective stimulation of the death receptor CD95 on the surface of normal, activated or malignant B cells expressing both, CD20 and CD95.

FIG. 1A: chemically hybridized bispecific (Fab')$_2$ fragment (herein also called bsFab$_2$). Bispecific Fab$_2$ fragments were prepared as described in Jung et al. Eur. J. Immunol. 21:2431, 1991. The parental antibodies used for chemical hybridization were the anti-CD20 antibody Rituximab (Roche) approved for the treatment of B-cell derived malignant lymphoma, and the anti-CD95 antibody Apo-1 purified from the supernatant of cultured hybridoma cells. Alternatively, the Apo-1 antibody can be purchased in purified form (BMS151) from eBioscience, San Diego, Calif. 92121.

FIG. 1B: recombinant bispecific Fab-single chain (herein also called bsFabXsc or NA-C20). NA-C20 contains a Fab, which is linked to an scFv using a monomeric CH2 domain as a linker.

The sequence of this antibody format, including those of the CD20 (2H7, murine and humanized) and CD95 antibodies (murine and humanized) are provided in FIG. 9E. The genetic construct encoding the antibody was stably transfected into Sp2/0 cells using standard techniques. The protein was purified from supernatants of transfected cells using affinity chromatography with kappa-select, purchased from GE-Healthcare, Life Sciences, Freiburg, Germany.

Figure 2:
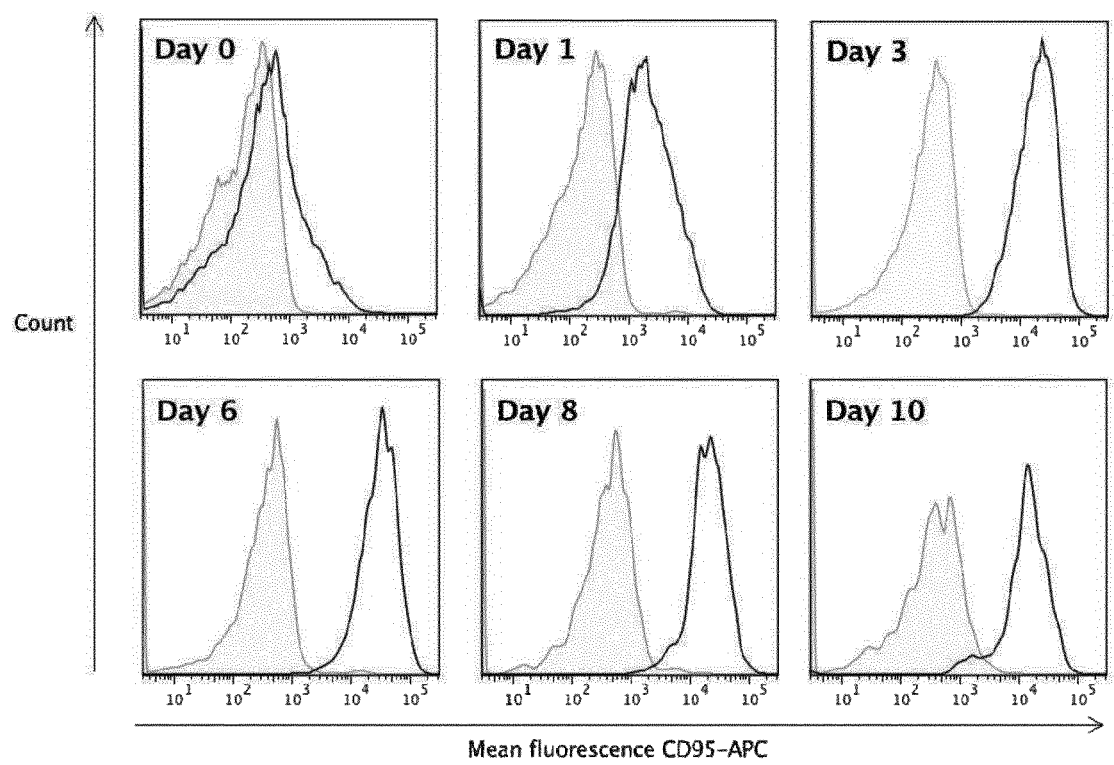

FIG. 2: Expression of CD95 on human B-cells activated with 1 μg/mL PWM.

Peripheral blood mononuclear cells (PBMC) of a normal healthy donor, isolated by density gradient centrifugation, were incubated with pokeweed mitogen (PWM, 1 μg/ml, Sigma Aldrich, Taufkirchen, Germany) for 6 days and washed. At the indicated time points cells were removed from the culture flasks and analyzed by flow cytometry. To this end cells were stained with a CD19 antibody or an isotype control antibody coupled to pacific blue, a CD95 antibody coupled to allophycocyanin (APC) and the 7-amino-actinomycin D (7-AAD) dye to clearly identify viable cells. Viable, CD19-positive cells were gated and analyzed. Antibodies were purchased from Biolegend, San Diego, Calif. 92121. Bright profiles were obtained with an isotype control-dark profiles with the CD95 antibody.

Conclusion: While CD95 is not detectable on resting B cells its expression rises after 1 day of PWM stimulation, reaches its maximum at day three and remains high up to day 10 despite washing of the cells at day 6.

Figure 3:
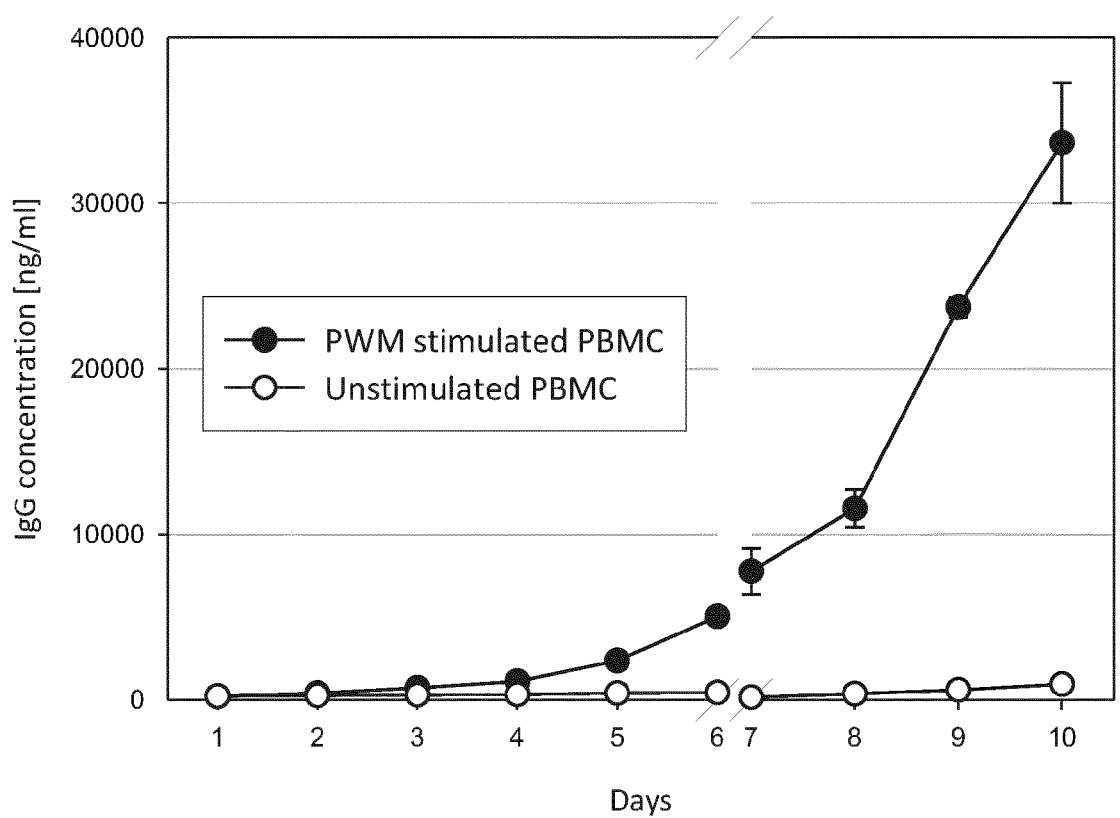

FIG. 3: Kinetic of IgG production by PWM activated B-cells.

Normal PBMC were stimulated with PWM (1 μg/ml). After various times aliquots of the culture supernatant were removed and analyzed by ELISA for human IgG content. Stimulation of PBMC with PWM (full circle) induces production of human IgG. Antibody production becomes detectable at day 4 and rises continuously up to day 10. Measurement of antibody production of unstimulated PBMC (open circle) serves as control.

Conclusion: IgG production becomes detectable after 5 days of PWM stimulation and rises continuously up to day 10.

Figure 4:
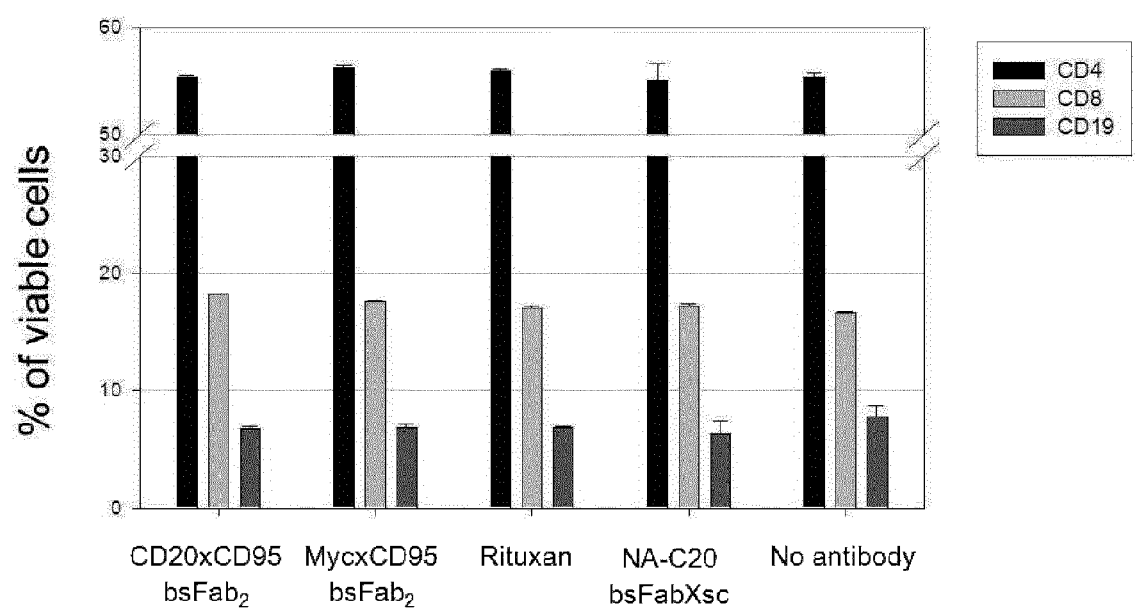

FIG. 4: Depletion of CD19+ B cells and CD4/CD8+ T-helper/killer cells from unstimulated PBMC Unstimulated PBMC were incubated for 4 days with the antibodies indicated (1 μg/ml), washed and analyzed by flow cytometry using a CD19 antibody coupled to pacific blue, a CD4 antibody coupled to fluorescein isothiocyanate (FITC), a CD8 antibody coupled to APC and the viability dye 7-AAD (Biolegend, San Diego, Calif. 92121). NA-C20 is the recombinant bispecific antibody depicted in FIG. 1B.

Conclusion: None of the indicated antibodies affects T cells or B cells in unstimulated PBMC cultures.

Figure 5:
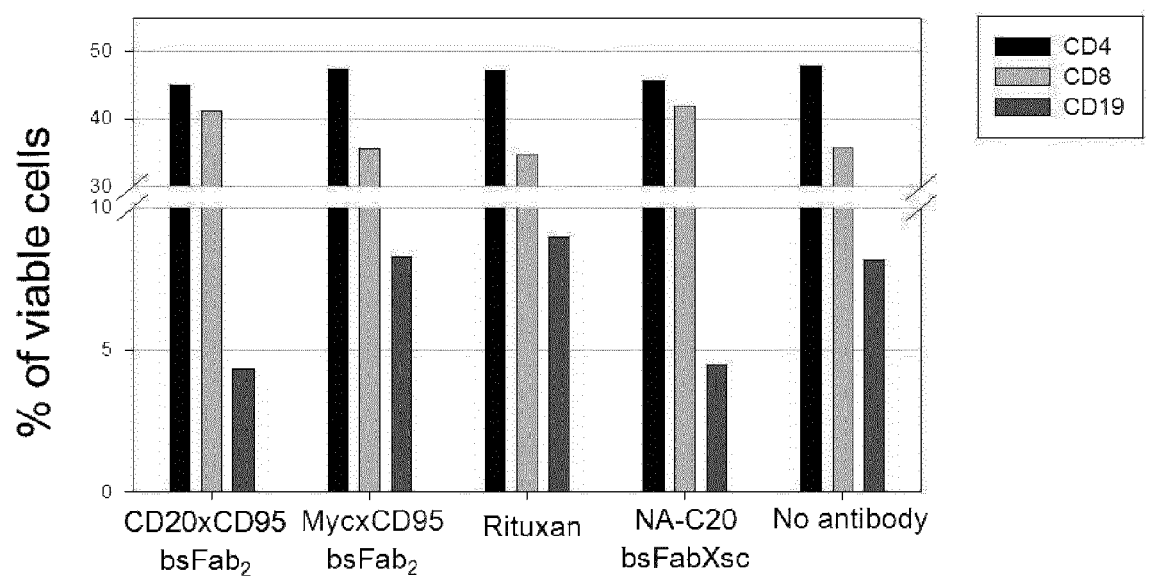

FIG. 5: Depletion of CD19+ B cells and CD4/CD8+ T-helper/killer cells from stimulated PBMC.

PBMC were stimulated for 6 days with pokeweed mitogen (PWM, Sigma-Aldrich, 1 µg/ml), washed and incubated for 4 days with the antibodies indicated (1 µg/ml). Cells were analyzed by flow cytometry at day 10 as described in FIG. 4. NA-C20 is the recombinant bispecific antibody in the bsFabXsc-format depicted in FIG. 1B.

Conclusion: The two bispecific CD20×CD95 antibodies induce depletion of B cells in PWM-stimulated PBMC. T cells are not affected. A chemically hybridized control antibody with Myc×CD95-specificity is ineffective.

Figure 6:
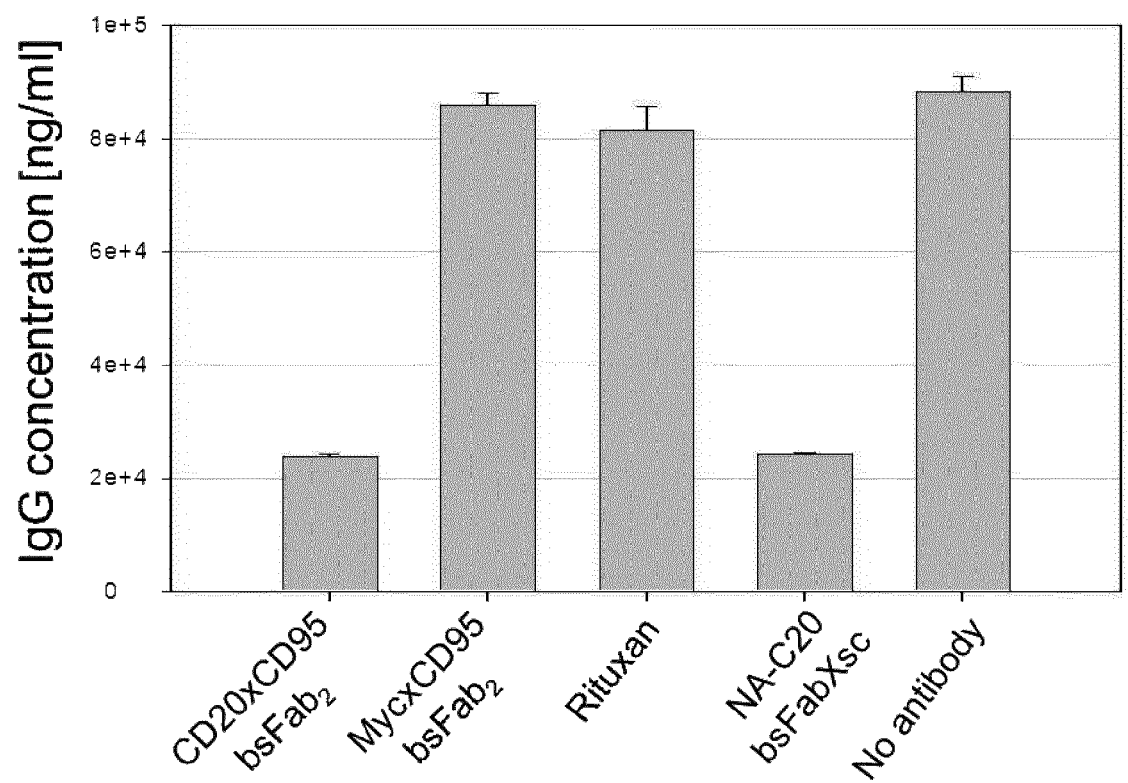

FIG. 6: Suppression of antibody production in vitro:

Human peripheral blood mononuclear cells (PBMC) were isolated from heparinized blood by density gradient centrifugation, seeded at $1 \times 10^6$ cells/ml in 6 well plates and stimulated with the lectin pokeweed mitogen (PWM, 1 µg/ml, Sigma Aldrich). At day 6 cells were washed and the indicated antibodies were added. At day 10, the amount of human IgG in the supernatant was measured by ELISA. NA-C20 is the recombinant bispecific antibody in the bsFabXsc-format depicted in FIG. 1B.

Conclusion: Both bispecific CD20×CD95 antibodies suppress IgG production by stimulated human PBMC. A chemically hybridized control antibody with Myc×CD95-specificities does not.

Figure 7A:
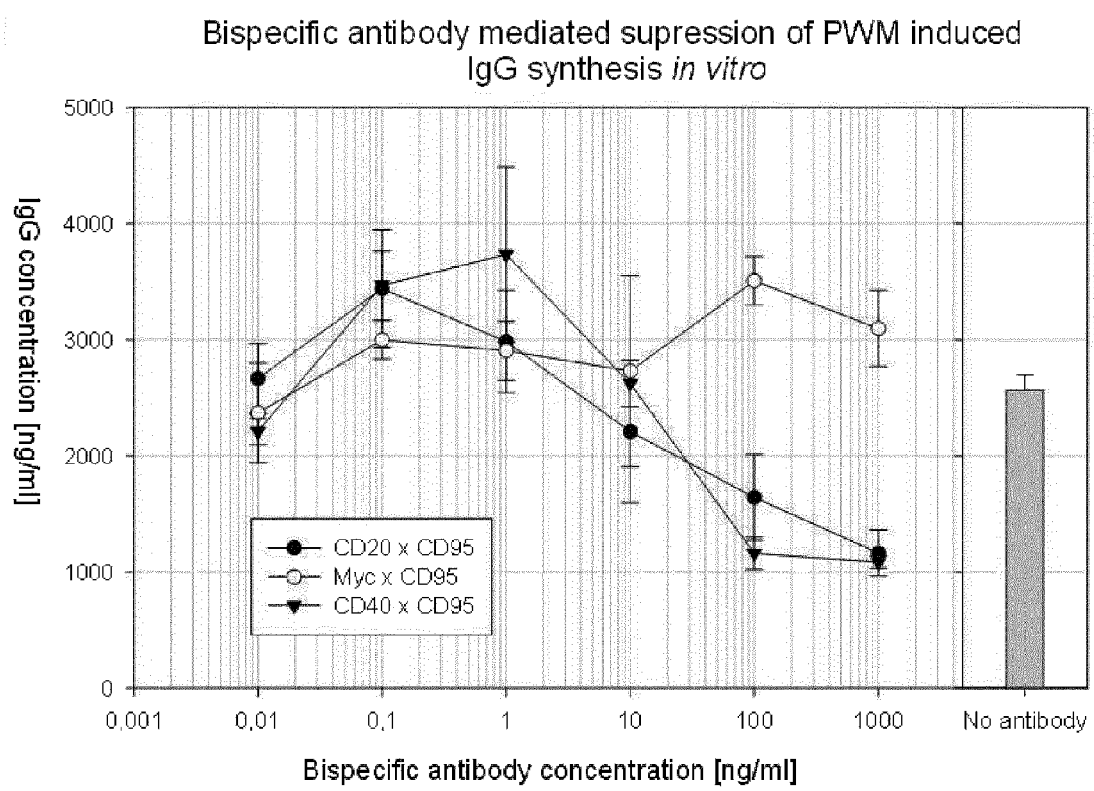
Figure 7B:
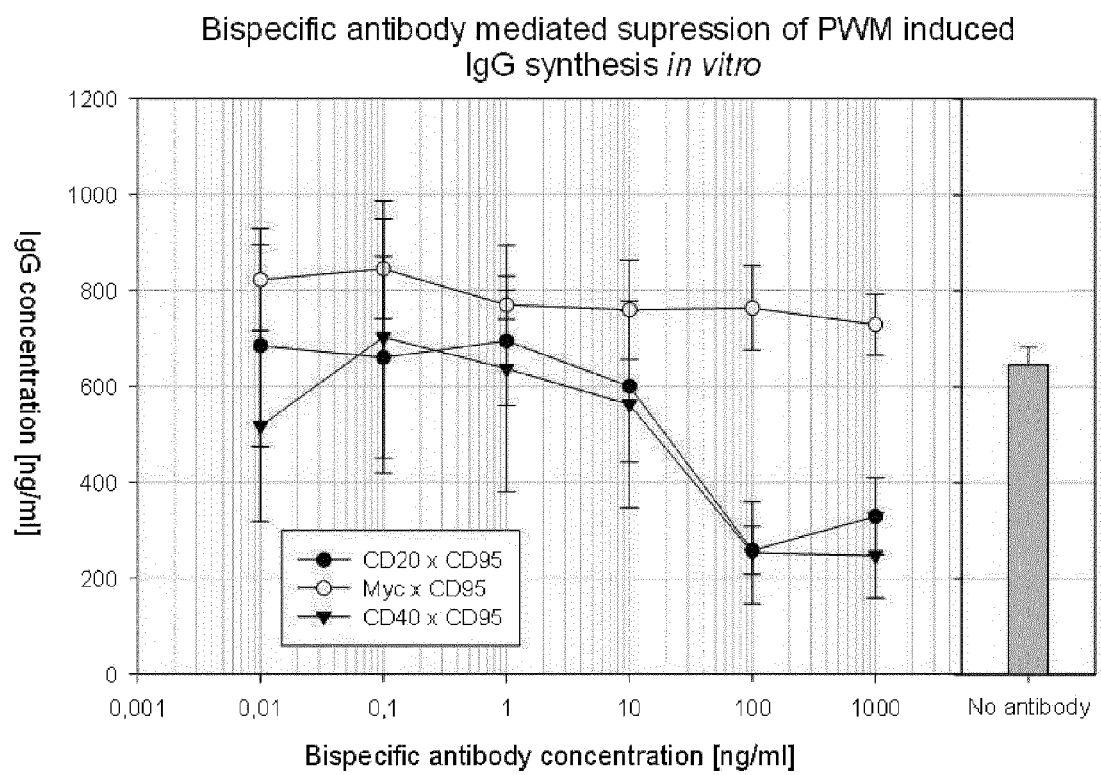
Figure 7C:
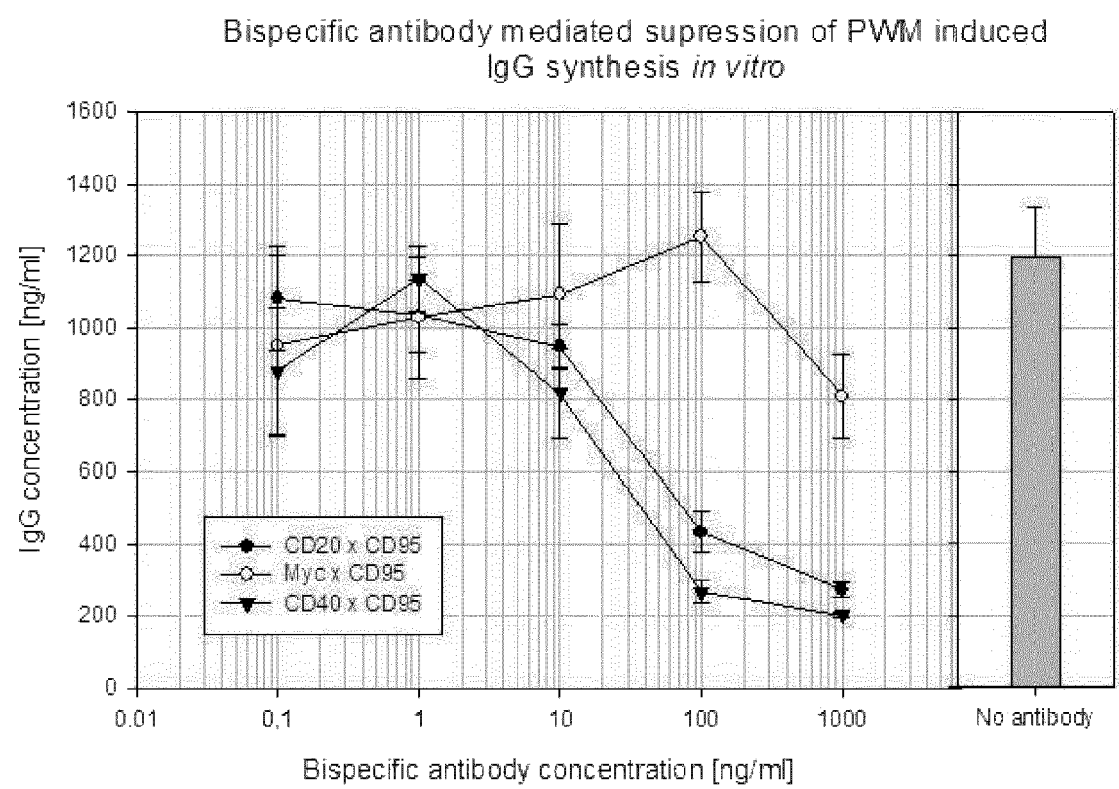

FIGS. 7A-7C: Bispecific antibody mediated suppression of PMW induced IgG synthesis in vitro. Human peripheral blood mononuclear cells (PBMC) of three different healthy donors (7A-7C) were isolated from heparinized blood by density gradient centrifugation, seeded at $1 \times 10^6$ cells/ml in 6 well plates and stimulated with the lectin pokeweed mitogen (PWM, 1 µg/ml Sigma Aldrich).

FIG. 7A: At day 6, cells from the first donor were washed and bispecific F(ab')$_2$ antibodies (i.e. the F(ab')$_2$ antibody format) were added. At day 10, the amount of human IgG in the supernatant was measured by ELISA. Bispecific antibodies tested were either specifically targeting CD20×CD95 (full circle) or CD40×CD95 (triangles). As a comparison, a bispecific antibody (i.e. the F(ab')$_2$ antibody format) with an unrelated target specificity directed to the intracellular myc-protein (myc×CD95) (open circle) was tested in parallel.

FIG. 7B: At day 6, cells from the second donor were washed and bispecific F(ab')$_2$ antibodies (i.e. the F(ab')$_2$ antibody format) were added. At day 10, the amount of human IgG in the supernatant was measured by ELISA. Bispecific antibodies tested were either specifically targeting CD20×CD95 (full circle) or CD40×CD95 (triangles). As a comparison, a bispecific antibody (i.e. the F(ab')$_2$ antibody format) with an unrelated target specificity direct to the intracellular myc-protein (myc×CD95) (open circle) was tested in parallel.

FIG. 7C: At day 6, cells from the third donor were washed and bispecific F(ab')$_2$ antibodies (i.e. the F(ab')$_2$ antibody format) were added. At day 10, the amount of human IgG in the supernatant was measured by ELISA. Bispecific antibodies tested were either specifically targeting CD20×CD95 (full circle) or CD40×CD95 (triangles). As a comparison, a bispecific antibody (i.e. the F(ab')$_2$ antibody format) with an unrelated target specificity direct to the intracellular myc-protein (myc×CD95) (open circle) was tested in parallel.

Conclusion:

Bispecific Fab2 antibodies with CD20×CD95 or CD40×CD95-specificity suppress IgG production by activated human B cells in vitro, antibodies with Myc×CD95-specificity do not.

Figure 8:
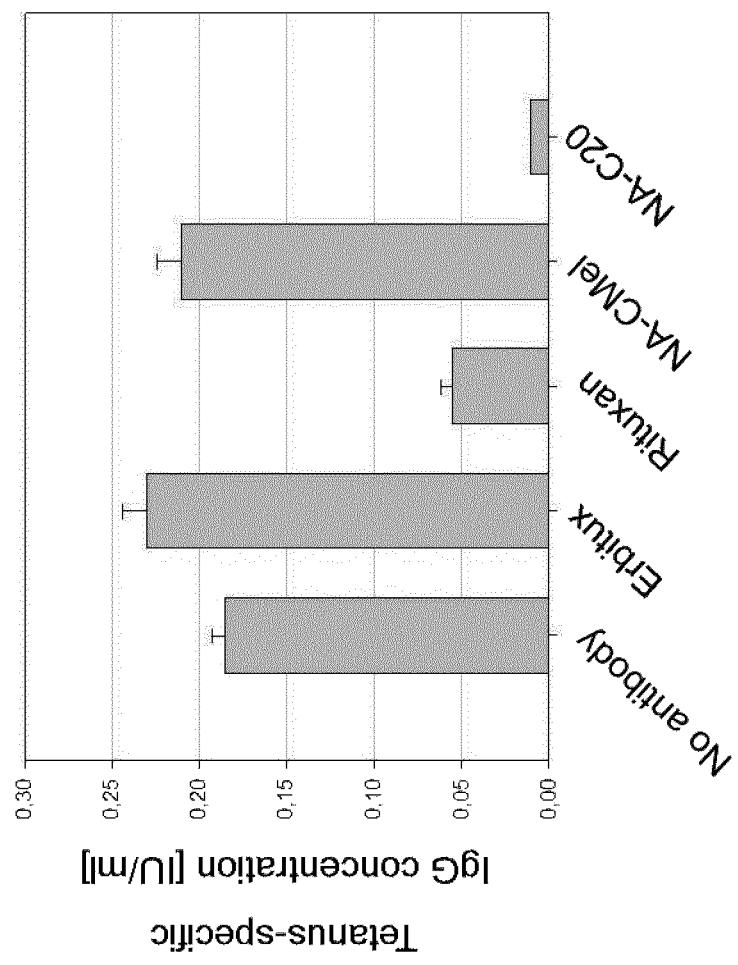

FIG. 8: Suppression of Tetanus Toxoid specific IgG production

PBMC of a donor, freshly vaccinated with tetanus toxoid, were stimulated with tetanus toxoid (25 ng/ml, Calbiochem, Merck Darmstadt, Germany) for 4 days, washed and incubated with the indicated antibodies (1 µg/ml) for 8 days. At day 12 the amount of specific anti-tetanus antibodies was determined by ELISA. NA-C20 is the recombinant bispecific CD20×CD95 antibody in the bsFabXsc-format depicted in FIG. 1B.

Conclusion: The recombinant bispecific CD20×CD95 antibody NA-C20 and the monospecific anti-CD20 antibody Rituxan suppress the production of specific anti-tetanus toxoid antibodies in vitro. Corresponding antibodies with unrelated target specificities directed to the EGF-receptor (Erbitux) and a melanoma associated proteoglycan (NA-CMel), respectively, are ineffective.

FIGS. 9A-9E: Sequence of exemplary antibody formats as referred to in the Examples.

FIG. 9A: Mouse VL and VH sequences (SEQ ID 1 and 5, respectively) of an antibody format with a binding site directed to CD95, CDR sequences are underlined (CDR1, CDR2, CDR3 of VL: SEQ ID 2-4; CDR1, CDR2, CDR3 of VH: SEQ ID 6-8).

FIG. 9B: VL and VH sequences (SEQ ID 9 and 10, respectively) of an antibody format with a binding site directed to CD95 (humanized), CDR sequences are underlined.

FIG. 9C: VL and VH sequences (SEQ ID 11 and 15, respectively) of an antibody format with a binding site directed to CD20 (murine, derived from the antibody 2H7 as described by Liu et al. The Journal of Immunology 139, 3521-3526 (1987), NCBI Accession M17953 and M17954), CDR sequences are underlined (CDR1, CDR2, CDR3 of VL: SEQ ID 12-14; CDR1, CDR2, CDR3 of VH: SEQ ID 16-18).

FIG. 9D: VL and VH sequences (SEQ ID 19 and 20, respectively) of an antibody format with a binding site directed to CD20 (humanized, derived from the antibody 2H7), CDR sequences are underlined.

FIG. 9E: Exemplary bispecific antibody formats CD95×CD20, chimeric and humanized versions: SEQ ID 21: chimeric version, light chain; SEQ ID 22: chimeric version heavy chain; SEQ ID 23: linker sequence; SEQ ID 24: humanized version light chain; SEQ ID 25: humanized version heavy chain.

DETAILED DESCRIPTION

The term "antibody format" as used herein shall refer to polypeptides or proteins that consist of or comprise antibody domains, which are understood as constant and/or variable domains of the heavy and/or light chains of immunoglobulins. The definition specifically refers to domains of the heavy and light chains of the variable region (such as dAb, Fd, VL, Vk, VH, VHH) and the constant region or individual domains of an intact antibody such as CH1, CH2, CH3, CH4, Cl and Ck. Vk or Vl is understood as VL, the variable domain of the light chain, kappa or lambda; likewise Cl or Ck the CL domain kappa or lambda. It is expressly understood that a reference to an antibody domain as used herein is understood to refer to any types or variants of such antibody domain. Thus, any reference to a VH domain as used herein, is understood to encompass any type of VH domain, including VHH.

Antibody domains may be of native structure or modified by mutagenesis or derivatization, e.g. to modify the antigen binding properties or any other property, such as stability or functional properties, such as binding to the Fc receptors FcRn and/or Fcgamma receptor. Polypeptide sequences are considered to be antibody domains, if comprising a beta-barrel structure consisting of at least two beta-strands of an antibody domain structure connected by a loop sequence.

The term "antibody format" shall particularly refer to polypeptides or proteins that may exhibit mono- or bi- or multi-specific, or mono-, bi- or multivalent binding properties, preferably at least two, more preferred at least three specific binding sites for epitopes of e.g. antigens, effector molecules or structures either of pathogen origin or of human structure, like self-antigens including cell-associated or serum proteins. The term antibody format as used according to the invention includes full-length antibodies or functional fragments of an antibody, such as Fab (herein understood to include Fab, F(ab) or F(ab')), (Fab')$_2$, scFv or other single chain dimers, e.g. of CH1/CL (kappa or lambda) domains, Fv, dimers like VH/VL, CH1/CL, CH2/CH2, CH3/CH3, or other derivatives or combinations thereof, e.g. single chains of pairs of antibody domains or chains of antibody domains linked to each other by a linker or hinge region, specifically an antibody format as depicted in FIG. 1A or 1B.

An antibody digested by papain yields three fragments: two Fab fragments and one Fc fragment. The term "Fab" is herein understood to include Fab, F(ab) or F(ab'), which may or may not include a hinge region. The Fab or F(ab') fragment is an antibody structure that still binds to antigens but is monovalent with no Fc portion. One of the preferred embodiments of the invention refers to an antibody format comprising an Fab fragment, which comprises the VH/VL domain pair and further two antibody constant domains, e.g. CL and CH1.

F(ab')$_2$ fragment antibodies are generated by pepsin digestion of whole IgG antibodies to remove most of the Fc region while leaving intact some of the hinge region. F(ab')$_2$ fragments have two antigen-binding F(ab') portions linked together, and therefore are divalent.

It is preferred that the antibody format of the present invention comprises at least variable domains to provide for the at least two specific binding site(s); and at least one, preferably at least 2, or at least three constant domains.

The term "antibody format" shall specifically include isolated antibody formats, herein understood to be substantially free of other antibody formats directed against different target antigens or comprising a different structural arrangement of antibody domains. Still, an isolated antibody format as used according to the invention may be comprised in a combination preparation, containing a combination of the isolated antibody format, e.g. with at least one other antibody format, such as monoclonal antibodies or antibody fragments having different specificities.

The antibody format as used herein may be a recombinant bispecific antibody format, which term includes all antibody formats that are prepared, expressed, created or isolated by recombinant means, such as antibodies originating from animals, e.g. mammalians including human, that comprises genes or sequences from different origin, e.g. humanized antibodies, or hybridoma derived antibodies. Further examples refer to antibody formats isolated from a host cell transformed to express the antibody format, or antibody formats isolated from a recombinant, combinatorial library of antibodies or antibody domains, or antibody formats prepared, expressed, created or isolated by any other means that involve splicing of antibody gene sequences to other DNA sequences.

It is understood that the term "antibody format" includes derivatives thereof. A derivative is any combination of one or more antibody domains or antibody formats of the invention and or a fusion protein in which any domain of the antibody format of the invention may be fused at any position of one or more other proteins, such as other antibodies or antibody formats, e.g. a binding structure comprising CDR loops, a receptor polypeptide, but also ligands, scaffold proteins, enzymes, toxins and the like. A derivative of the modular antibody of the invention may also be obtained by association or binding to other substances by various chemical techniques such as covalent coupling, electrostatic interaction, di-sulphide bonding etc. The other substances bound to the immunoglobulins may be lipids, carbohydrates, nucleic acids, organic and inorganic molecules or any combination thereof (e.g. PEG, prodrugs or drugs). The term derivative also includes fragments, variants, analogs or homologs of antibody formats, which are functional and may serve as functional equivalents, e.g. binding to the specific targets and with functional properties, such as IgG inhibitory activity or apoptotic activity. The preferred derivatives still are functional with regard to the antigen binding, the apoptotic activity and/or the activity to inhibit IgG production by auto-reactive B-cells.

The term "active Fc moiety" as used herein shall refer to an Fc fragment of an antibody that comprises at least two, preferably at least four constant antibody domains, e.g. CH2 and CH3 antibody domains, or modifications, derivatives, combinations or parts of constant antibody domains that are still functional by Fc effector function. Fc effector functions are understood in the following way. Antibodies comprising an active Fc moiety typically confer cytotoxic activity. When bound to an antigen, the Fc part mediates antibody-dependent cellular cytotoxicity (ADCC) and/or complement-dependent cytotoxicity (CDC) by its activity on effector cells resulting in activation of cytotoxic T-cells or cells which mediate ADCC or CDC. Functionally active Fc moieties therefore bind to effector cells via an Fcgamma receptor (FCGR) binding site.

Antibody formats according to the present invention are devoid of an active Fc moiety, thus, either composed of antibody domains that do not have an FCGR binding site, specifically including any antibody formats devoid of a chain of CH2 and CH3 domains, or comprising an Fc moiety lacking Fc effector function, e.g. by modifications to reduce Fc effector functions, in particular to abrogate or reduce ADCC and/or CDC activity. Such modifications may be effected by mutagenesis, e.g. mutations in the FCGR binding site or by derivatives or agents to interfere with ADCC and/or CDC activity of an antibody format, so to achieve reduction of Fc effector function or lack of Fc effector function, which is typically understood to refer to Fc effector function of less than 10% of the unmodified (wild-type) format, preferably less than 5%, as measured by ADCC and/or CDC activity. Specific examples refer to antibody formats comprising an Fc region, in which one or more alterations have been made in order to change functional or pharmacokinetic properties of the antibodies, e.g. by substitutions in one or more of the amino acid residues located in the Fc region responsible for mediating Fc effector function, e.g. mutations in the N-terminal region of the CH2 domain.

The term "autoreactive B-cell" and "autoreactive B-cell disorder" as used herein is understood in the following way. Autoreactive B cells are part of the naive B cell repertoire, and central in the pathogenesis of autoimmune diseases not only by producing autoantibodies but also by secreting cytokines and by presenting autoantigens. An autoreactive B-cell disorder is meant to refer to a disease condition that may be ameliorated by the administration of a pharmaceutical composition comprising an antibody format of the present invention. In diseases associated with an autoreactive B-cell disorder, like B cell-mediated autoimmune diseases, there is typically an aberrant negative selection and activation of autoreactive B cells.

Autoimmune diseases specifically are understood as disorders arising from reactions directed against a subject's own tissues or organs, typically antibody reactions with self-antigens. Among the various clinical and laboratory markers indicating autoimmune diseases there are hypergammaglobulinemia, high levels of autoantibodies, antigen-antibody complex deposits in tissues, clinical benefit from corticosteroid or immunosuppressive treatments, and lymphoid cell aggregates in affected tissues.

The antibody format according to the present invention allows the modulation of the B cell repertoire to reduce autoreactivity of B cells. The modulation is more specific than that achieved by monospecific antibodies, since only activated B cell expressing CD95 and not resting B cells lacking it are affected. It could be shown that the antibody format according to the invention induced apoptosis of activated B-cells, and further suppressed activation induced IgG production and inhibited IgG synthesis of activated B-cells. Thus, auto-reactive B-cells producing IgG antibodies directed against autoimmune targets, such as auto-antigens, may be effectively reduced.

By the bispecific antibody format of the present invention, specifically the CD20×CD95 bispecific, not only malignant B cells, but also activated normal (benign) B cells that express the CD95 death receptor could be targeted and depleted. In contrast, resting B cells were not targeted, no effect could be seen with such normal B cells. This indicates that activated B cells are CD95 sensitive to undergo apoptotic cell death after incubation with bispecific CD20×CD95 antibodies of the described kind.

Depleting activated B cells suppresses antibody production. This was surprising, because the terminally differentiated antibody-producing cells, i.e. plasma cells, do not express CD20. Suppressing the activated precursor B cells is obviously sufficient to suppress antibody production.

Suppressing antibody production by the bispecific antibody formats of the invention is preferable over the use of established monospecific CD20 antibodies like rituximab (Rituxan®), which depletes all CD20 expressing B cells, without differentiating autoreactive or activated B cells from normal or resting B cells.

The term "binding site" as used herein with respect to an antibody or antibody format according to the present invention refers to a molecular structure capable of binding interaction with an antigen. Typically the binding site is located within the complementary determining region (CDR) of an antibody, herein also called "a CDR binding site", which is a specific region with varying structures conferring binding function to various antigens. The varying structures can be derived from natural repertoires of antibodies, e.g. murine or human repertoires, or may be recombinantly or synthetically produced, e.g. by mutagenesis and specifically by randomization techniques. These include mutagenized CDR regions, loop regions of variable antibody domains, in particular CDR loops of antibodies, such as CDR1, CDR2 and CDR3 loops of any of VL and/or VH antibody domains. The antibody format as used according to the invention typically comprises one or more CDR binding sites, each specific to an antigen.

The term "specific" or "bispecific" as used herein shall refer to a binding reaction which is determinative of the cognate ligand of interest in a heterogeneous population of molecules. Thus, under designated conditions, e.g. immunoassay conditions, the antibody format that specifically binds to its particular target does not bind in a significant amount to other molecules present in a sample.

A specific binding site is typically not cross-reactive with other targets. Still, the specific binding site may specifically bind to one or more epitopes, isoforms or variants of the target, or be cross-reactive to other related target antigens, e.g., homologs or analogs.

The specific binding means that binding is selective in terms of target identity, high, medium or low binding affinity or avidity, as selected. Selective binding is usually achieved if the binding constant or binding dynamics is at least 10 fold different, preferably the difference is at least 100 fold, and more preferred a least 1000 fold.

The bispecific antibody format of the present invention specifically comprises two or more binding sites, possibly 3 or 4 binding sites with specific binding properties, wherein at least two different target antigens are recognized by the antibody format. Thus, an exemplary bispecific antibody format may comprise two binding sites, wherein each of the binding sites is capable of specifically binding a different antigen, e.g. a death receptor and a cell surface antigen of a B-cell. Where the bispecific antibody format comprises more than two binding sites, it may be directed against more than two different target antigens and/or comprise more than one valencies to specifically bind to a single or the same type of target antigen.

The term "monovalent" as used herein with respect to a binding site of an antibody or antibody format shall refer to a molecule comprising only one binding site directed against a target antigen. The term "valency" is thus understood as the number of binding sites directed against the same target antigen, either specifically binding the same or different epitopes of an antigen. Where an antibody or antibody format as used according to the inventions comprises two or more binding sites, e.g. 2, 3 or 4 binding sites against the same target antigen, which specifically are directed to the same or different epitopes of an antigen, this is called bivalency or multivalency.

The antibody format as used according to the present invention is understood to comprise a monovalent binding site specifically binding a death receptor target and at least one further binding site to specifically bind a cell surface antigen expressed on B-cells, in particular autoreactive B-cells. Thus, it is understood to be monovalent with respect to the death receptor binding, and mono-, bi- or multivalent with respect to the cell surface antigen binding.

The term "antigen" as used herein interchangeably with the terms "target" or "target antigen" shall refer to a whole target molecule or a fragment of such molecule recognized by an antibody binding site. Specifically, substructures of an antigen, e.g. a polypeptide or carbohydrate structure, generally referred to as "epitopes", e.g. B-cell epitopes or T-cell epitope, which are immunologically relevant, may be recognized by such binding site. The term "epitope" as used herein shall in particular refer to a molecular structure which may completely make up a specific binding partner or be part of a specific binding partner to a binding site of an antibody format of the present invention. An epitope may either be composed of a carbohydrate, a peptidic structure, a fatty acid, an organic, biochemical or inorganic substance or derivatives thereof and any combinations thereof. If an epitope is comprised in a peptidic structure, such as a peptide, a polypeptide or a protein, it will usually include at least 3 amino acids, preferably 5 to 40 amino acids, and more preferably between about 10-20 amino acids. Epitopes can be either linear or conformational epitopes. A linear epitope is comprised of a single segment of a primary sequence of a polypeptide or carbohydrate chain. Linear epitopes can be contiguous or overlapping. Conformational epitopes are comprised of amino acids or carbohydrates brought together by folding the polypeptide to form a tertiary structure and the amino acids are not necessarily adjacent to one another in the linear sequence.

The term "cell surface antigen" with respect to a B-cell as used herein shall refer to an antigen expressed on the surface of a B cell, preferably a mature, activated or auto-reactive B-cell that can be targeted with an antagonist that binds thereto. Exemplary B-cell surface markers include the CD19, CD20 and CD40.

The B-cell surface antigen of particular interest is preferentially highly expressed on the surface of auto-reactive B cells, preferentially more than 10.000 molecules per cell.

A binding site specifically binding to an antigen selected from CD19, CD20 and CD40, may be derived from a commercially available monoclonal antibody directed against the antigen, e.g. rituximab or ocrelizumab directed against CD20. Specifically a binding site derived from any of the anti-CD20 antibody formats as exemplified in FIG. 9 may be used.

The term "CD19" includes any variants, isoforms and species homologs of human CD19 which are naturally expressed by cells or are expressed on cells transfected with the CD19 gene.

The term "CD20" includes any variants, isoforms and species homologs of human CD20 which are naturally expressed by cells or are expressed on cells transfected with the CD20 gene.

The term "CD40" includes any variants, isoforms and species homologs of human CD40 which are naturally expressed by cells or are expressed on cells transfected with the CD40 gene.

The term "death receptor" with respect to a B-cell as used herein shall refer to an antigen derived from a receptor on the surface of cells that leads to programmed cell death by one or more apoptosis pathways. Exemplary death receptors are expressed on activated B-cells, and include e.g. CD95, the TRAIL receptors, e.g. TRAIL-R1 or TRAIL-R2, and the TNF receptors. In contrast to activated B cells, CD95 is not expressed on normal resting B cells.

CD95 is also known as Fas or Apo-1, and member of the tumor necrosis factor receptor superfamily. A binding site specifically binding to CD95 may be derived from antibodies directed to CD95, such as the clones APO-1 or LT95 and DX 2 distributed by Acris Antibodies, Herford, Germany. Specifically a binding site derived from any of the anti-CD95 antibody formats as exemplified in FIG. 9 may be used.

The term "CD95" includes any variants, isoforms and species homologs of human CD95 which are naturally expressed by cells or are expressed on cells transfected with the CD95 gene.

The term "variants" shall refer to mutants, e.g. obtained by site-directed mutagenesis methods, in particular to delete, exchange, introduce inserts into a specific antibody region or chemically derivatize an amino acid sequence, in the constant domains to engineer the antibody effector function or half-life, or in the variable domains to improve antigen-binding properties, e.g. by affinity maturation techniques. Any of the known mutagenesis methods may be employed, including point mutations at desired positions, e.g. obtained by randomisation techniques. In some cases positions are chosen randomly, e.g. with either any of the possible amino acids or a selection of preferred amino acids to randomise the antibody sequences. The term "variant" shall specifically encompass functionally active variants.

The term "functionally active variant" of a molecule, such as the antibody as used herein, means a sequence resulting from modification of this sequence (a parent sequence) by insertion, deletion or substitution of one or more amino acids, or chemical derivatization of one or more amino acid residues, or nucleotides within the sequence or at either or both of the distal ends of the sequence, and which modification does not affect (in particular impair) the activity of this sequence. In the case of a binding site having specificity to a selected target antigen, the functionally active variant of a molecule would still have the predetermined binding specificity, though this could be changed, e.g. to change the fine specificity to a specific epitope, the affinity, the avidity, the Kon or Koff rate, etc.

Functionally active variants may be obtained by changing the sequence of a parent antibody format, e.g. any of the sequences of FIG. 9, e.g. the NA-C20 sequence of FIG. 9E i) or ii), and are characterized by having a biological activity similar to that displayed by the respective sequence, including the ability to bind CD20 and/or CD95 or to target activated or auto-reactive B-cells.

The functionally active variant of the antibody format preferably has substantially the same biological activity, as determined by a specific binding assay or functional test to target activated or auto-reactive B-cells. The term "substantially the same biological activity" as used herein refers to the activity as indicated by substantially the same activity being at least 50%, at least 60%, at least 70%, at least 80%, at least 90%, at least 95%, at least 98% or even at least 100% or at least 110%, or at least 120%, or at least 130%, or at least 140%, or at least 150%, or at least 160%, or at least 170%, or at least 180%, or at least 190%, e.g. up to 200% of the activity as determined for the parent antibody format, e.g. the recombinant bispecific antibody format NA-C20 of FIG. 9B.

In a preferred embodiment the functionally active variant
a) is a biologically active fragment of the molecule, the fragment comprising at least 50% of the sequence of the molecule, preferably at least 70%, more preferably at least 80%, still more preferably at least 90%, even more preferably at least 95% and most preferably at least 97%, 98% or 99%;

b) is derived from the molecule by at least one amino acid substitution, addition and/or deletion, wherein the functionally active variant has a sequence identity to the molecule or part of it, such as an antibody of at least 50% sequence identity, preferably at least 60%, more preferably at least 70%, more preferably at least 80%, still more preferably at least 90%, even more preferably at least 95% and most preferably at least 97%, 98% or 99%; and/or c) consists of the molecule or a functionally active variant thereof and additionally at least one amino acid or nucleotide heterologous to the polypeptide or the nucleotide sequence, preferably wherein the functionally active variants are derived from any of the naturally occurring or recombinant anti-CD19, anti-CD20, anti-CD40 and/or anti-CD95 antibodies.

In one preferred embodiment of the invention, the functionally active variant of the antibody according to the invention is essentially identical to the variant described above, but differs from its polypeptide or the nucleotide sequence, respectively, in that it is derived from a homologous sequence of a different species. These are referred to as naturally occurring variants.

The invention specifically provides for chimeric, humanized or human sequences and functionally active variants of a parent antibody format comprising such chimeric, humanized or human sequences.

The term "chimeric" as used with respect to an antibody format of the invention refers to those antibodies wherein one portion of each of the amino acid sequences of heavy and light chains is homologous to corresponding sequences in antibodies derived from a particular species or belonging to a particular class, while the remaining segment of the chain is homologous to corresponding sequences in another species or class. Typically the variable region of both light and heavy chains mimics the variable regions of antibodies derived from one species of mammals, while the constant portions are homologous to sequences of antibodies derived from another. For example, the variable region can be derived from presently known sources using readily available B-cells or hybridomas from non-human host organisms in combination with constant regions derived from, for example, human cell preparations.

The term "humanized" as used with respect to an antibody format of the invention refers to a molecule having an antigen binding site that is substantially derived from an immunoglobulin from a non-human species, wherein the remaining immunoglobulin structure of the molecule is based upon the structure and/or sequence of a human immunoglobulin. The antigen binding site may either comprise complete variable domains fused onto constant domains or only the complementarity determining regions (CDR) grafted onto appropriate framework regions in the variable domains. Antigen-binding sites may be wild-type or modified, e.g. by one or more amino acid substitutions, preferably modified to resemble human immunoglobulins more closely. Some forms of humanized antibodies preserve all CDR sequences (for example a humanized mouse antibody which contains all six CDRs from the mouse antibody). Other forms have one or more CDRs which are altered with respect to the original antibody.

The term "human" as used with respect to an antibody format of the invention, is understood to include antibodies having variable and constant regions derived from human germline immunoglobulin sequences. The human antibody formats of the invention may include amino acid residues not encoded by human germline immunoglobulin sequences (e.g., mutations introduced by random or site-specific mutagenesis in vitro or by somatic mutation in vivo), for example in the CDRs. Human antibody formats of the invention include antibodies isolated from human immunoglobulin libraries or from animals transgenic for one or more human immunoglobulin.

The term "functionally active variant" also includes naturally occurring allelic variants, as well as mutants or any other non-naturally occurring variants. As is known in the art, an allelic variant is an alternate form of a (poly) peptide that is characterized as having a substitution, deletion, or addition of one or more amino acids that does essentially not alter the biological function of the polypeptide.

Functionally active variants may be obtained by sequence alterations in the polypeptide or the nucleotide sequence, e.g. by one or more point mutations, wherein the sequence alterations retains a function of the unaltered polypeptide or the nucleotide sequence, when used in combination of the invention. Such sequence alterations can include, but are not limited to, (conservative) substitutions, additions, deletions, mutations and insertions.

A CDR variant includes an amino acid sequence modified by at least one amino acid, wherein said modification can be chemical or a partial alteration of the amino acid sequence, which modification permits the variant to retain the biological characteristics of the unmodified sequence. For example, the variant is a functional variant which binds to CD19, CD20, CD40 or CD95. A partial alteration of the CDR amino acid sequence may be by deletion or substitution of one to several amino acids, e.g. 1, 2, 3, 4 or 5 amino acids, or by addition or insertion of one to several amino acids, e.g. 1, 2, 3, 4 or 5 amino acids, or by a chemical derivatization of one to several amino acids, e.g. 1, 2, 3, 4 or 5 amino acids, or combination thereof. The substitutions in amino acid residues may be conservative substitutions, for example, substituting one hydrophobic amino acid for an alternative hydrophobic amino acid.

Conservative substitutions are those that take place within a family of amino acids that are related in their side chains and chemical properties. Examples of such families are amino acids with basic side chains, with acidic side chains, with non-polar aliphatic side chains, with non-polar aromatic side chains, with uncharged polar side chains, with small side chains, with large side chains etc.

A point mutation is particularly understood as the engineering of a polynucleotide that results in the expression of an amino acid sequence that differs from the non-engineered amino acid sequence in the substitution or exchange, deletion or insertion of one or more single (non-consecutive) or doublets of amino acids for different amino acids.

Preferred point mutations refer to the exchange of amino acids of the same polarity and/or charge. In this regard, amino acids refer to twenty naturally occurring amino acids encoded by sixty-four triplet codons. These 20 amino acids can be split into those that have neutral charges, positive charges, and negative charges:

The "neutral" amino acids are shown below along with their respective three-letter and single-letter code and polarity:

Alanine: (Ala, A) nonpolar, neutral;
Asparagine: (Asn, N) polar, neutral;
Cysteine: (Cys, C) nonpolar, neutral;
Glutamine: (Gln, Q) polar, neutral;
Glycine: (Gly, G) nonpolar, neutral;
Isoleucine: (Ile, I) nonpolar, neutral;
Leucine: (Leu, L) nonpolar, neutral;
Methionine: (Met, M) nonpolar, neutral;
Phenylalanine: (Phe, F) nonpolar, neutral;
Proline: (Pro, P) nonpolar, neutral;
Serine: (Ser, S) polar, neutral;
Threonine: (Thr, T) polar, neutral;
Tryptophan: (Trp, W) nonpolar, neutral;
Tyrosine: (Tyr, Y) polar, neutral;
Valine: (Val, V) nonpolar, neutral; and
Histidine: (His, H) polar, positive (10%) neutral (90%).
The "positively" charged amino acids are:
Arginine: (Arg, R) polar, positive; and
Lysine: (Lys, K) polar, positive.
The "negatively" charged amino acids are:
Aspartic acid: (Asp, D) polar, negative; and
Glutamic acid: (Glu, E) polar, negative.

"Percent (%) amino acid sequence identity" with respect to the polypeptide sequences identified herein is defined as the percentage of amino acid residues in a candidate sequence that are identical with the amino acid residues in the specific polypeptide sequence, after aligning the sequence and introducing gaps, if necessary, to achieve the maximum percent sequence identity, and not considering any conservative substitutions as part of the sequence identity. Those skilled in the art can determine appropriate parameters for measuring alignment, including any algorithms needed to achieve maximal alignment over the full length of the sequences being compared.

The term "subject" as used herein shall refer to a warm-blooded mammalian, particularly a human being. A subject in need of prophylaxis or treatment of an autoreactive B-cell disorder specifically may be a patient suffering from early stage or late stage disease, or else subject predisposed of such disease, e.g. by genetic predisposition.

Therefore, the subject matter of the present invention is based on the surprising finding that exemplary bispecific antibody constructs, specifically binding to CD95 and CD19, CD20 or CD40 on the surface of activated B-cells, specifically suppresses IgG production and inhibits IgG synthesis, thereby reducing the generation of IgG levels in a subject and reducing autoimmune reactions in the subject. For the recombinant bispecific antibody NA-C20 described in this invention and depicted in FIG. 1B it is demonstrated that it suppresses not only antibody production by polyclonally activated B cells but more specifically activated B cells which produce specific antibody against tetanus toxoid.

It was previously described that bispecific antibodies with specificity for CD20 and the death receptor CD95 are capable of inducing CD95 mediated apoptosis in CD20-positive lymphoma cells. It surprisingly turned out that CD20×CD95 hybrid antibodies of the invention induce apoptosis in pokeweed mitogen (PWM) activated B cells expressing CD95, but not in resting cells lacking it. Antibody production induced by PWM in vitro is profoundly inhibited. These results indicate that bispecific CD20×CD95 antibodies of the invention may be used for the treatment of antibody mediated autoimmune disease. Compared to monospecific CD20 antibodies, these reagents offer a new effector principle and specificity for activated rather than resting B cells.

Further, the capability of bispecific CD20×CD95 antibodies of the invention and specific antibody formats to kill activated human B-cells in vitro was determined and compared with the anti-CD20 antibody rituximab.

The exemplary bispecific antibody formats according to the invention were capable of targeting CD20 and CD95-bearing cells, triggering the CD95 death receptor. Increased presence of CD20/CD95 positive, activated B cells is commonly associated with flares in lupus and rheumatoid arthritis. The involvement of activated B cells in multiple sclerosis (MS) is also increasingly accepted, as they are involved, e.g. in T-cell recruitment and activation, cytokine release and antibody production.

In vitro studies have shown that exemplary bispecific antibody formats of the invention can downregulate the production of immunoglobulins by activated human B-cells. It was found to be highly selective, thereby avoiding side effects by reducing unspecific reactions.

The suppression of IgG production by activated B-cells and the inhibition of IgG synthesis by the antibody formats according to the invention is understood as "IgG inhibitory activity". Such IgG inhibitory activity is referring to activated B-cells, in particular auto-reactive B-cells, and intended to include any measurable decrease in the IgG level, specifically the reduction of autoimmune antibody production, as compared to the IgG production of the same cells not in contact with the antibody format of the present invention, e.g., the IgG reduction in a test system employing activated B-cells, by at least about 10%, 20%, 30%, 40%, 50%, 60%, 70%, 80%, 90%, 99%, or 100%.

According to a specific embodiment, the antibody formats of the invention have apoptotic activity, i.e. direct cytotoxic activity against the target B-cells independent of immune-effector cells, such as NK cells. Specifically, the antibody formats of the invention have apoptotic activity, as measured in a standard apoptosis assay, e.g. as measured in a standard DNA fragmentation assay.

The apoptotic activity is preferably measured using standard methods of determinating dying and/or dead cells. In order to measure apoptosis, cytotoxicity assays can be employed. These assays can be radioactive and non-radioactive assays that measure increases in plasma membrane permeability, since dying cells become leaky, or colorimetric assays that measure reduction in the metabolic activity of mitochondria. Mitochondria in dead cells cannot metabolize dyes, while mitochondria in live cells can.

One can also measure early indicators for apoptosis such as alterations in membrane asymmetry resulting in occurrence of phosphatidylserine on the outside of the cell surface (Annexin V based assays). Alternatively, later stages of apoptosis, such as activation of caspases can be measured in populations of cells or in individual cells. In addition, measurement of release of cytochrome C and AIF into cytoplasm by mitochondria or fragmentation of chromosomal DNA can be determined.

Terminal deoxynucleotidyl transferase dUTP nick end labeling (TUNEL) is a common method for detecting DNA fragmentation that results from apoptotic signaling cascades. The assay relies on the presence of nicks in the DNA which can be identified by terminal deoxynucleotidyl transferase, an enzyme that will catalyze the addition of bromolated dUTPs that are secondarily detected with a specific labelled antibody.

The preferred apoptotic activity of the antibody format according to the invention amounts to at least 20% of cytolysis, preferably at least 30%, more preferred at least 40%, even more preferred at least 50%, as measured in a respective ex vivo cell killing assay; e.g. measuring survival of B cells after incubation with bispecific antibodies by flow cytometry.

Due to the lack of Fc effector function, the antibody format of the present invention specifically would not have a significant cytotoxic activity in the presence of immune-effector cells as measured in a standard ADCC or CDC assay, e.g. employing cells expressing the receptor target on the cell surface.

The low cytotoxic activity as determined by either of an ADCC or CDC assay may be shown for any antibody format of the invention, if there is no significant increase in the percentage of cytolysis as compared to a control. The lack of Fc effector function is typically determined if the cytotoxic activity as measured by the absolute percentage increase of the ADCC and/or CDC activity, is preferably lower than 10%, preferably lower than 5%, more preferably lower than 3%.

Preferably, an antibody format is used that binds to one or both of the target antigens with a high affinity, in particular with a high on and/or a low off rate, or a high avidity of binding. The binding affinity of an antibody is usually characterized in terms of the concentration of the antibody, at which half of the antigen binding sites are occupied, known as the dissociation constant (Kd, or KD). Usually a binder is considered a high affinity binder with a $Kd<10^{-8}$ M, preferably a $Kd<10^{-9}$ M, even more preferred is a $Kd<10^{-10}$ M.

Yet, in an alternatively preferred embodiment the individual antigen binding affinities are of medium affinity, e.g. with a Kd of less than $10^{-6}$ M and up to $10^{-8}$ M, e.g. when binding to at least two antigens.

Bispecific monoclonal antibody formats of the invention can be produced by a variety of techniques, including chemical hybridization of two Fab-fragments resulting in bispecific $Fab_2$ fragments ($(Fab')_2$, $bsFab_2$) and recombinant antibody technology, optionally employing hybridoma or libraries of human antibody sequences. The data provided in the examples were obtained with $bsFab_2$-fragments ($(Fab')_2$) or the recombinant bsFabXsc-format depicted in FIG. 1B. Recombinant antibody technology is preferred since it allows reproducible production by transfected cells and simplified purification.

The antibody formats of the present invention are preferably used in a pharmaceutical composition. Pharmaceutical compositions are contemplated wherein the antibody format of the present invention and one or more therapeutically active agents are formulated. Stable formulations of the antibody formats of the present invention are prepared for storage by mixing the antibody format having the desired degree of purity optionally with pharmaceutically acceptable carriers, excipients or stabilizers, in the form of lyophilized formulations, aqueous solutions or oil-in-water emulsions Typically such compositions comprise a pharmaceutically acceptable carrier as known and called for by acceptable pharmaceutical practice, see e.g. Remingtons Pharmaceutical Sciences, 16th edition (1980) Mack Publishing Co. Examples of such carriers include sterilized carriers such as saline, Ringers solution or dextrose solution, optionally buffered with suitable buffers to a pH within a range of 5 to 8.

The formulations to be used for in vivo administration will need to be sterile. This is readily accomplished by filtration through sterile filtration membranes or other suitable methods.

Administration of the pharmaceutical composition comprising the antibody formats of the present invention may be done in a variety of ways, including systemic or parenteral administration, preferably in the form of a sterile aqueous solution, e.g. by the intravenous, intramuscular or subcutaneous route, but also orally, intranasally, intraotically, transdermally, mucosal, topically (e.g., gels, salves, lotions, creams, etc.), intraperitoneally, intramuscularly, intrapulmonary, vaginally, parenterally, rectally or intraocularly. Thus, the invention provides for the antibody format in a respective formulation suitable for such use.

The present invention includes treatment with a pharmaceutical preparation, containing as active substance the antibody formats of the invention in a therapeutically effective amount. In particular, a pharmaceutically acceptable formulation of the antibody format is compatible with the treatment of a subject in need thereof.

The term "therapeutically effective amount", used herein interchangeably with any of the terms "effective amount" or "sufficient amount" of the antibody format of the present invention, is a quantity or activity sufficient to, when administered to the subject effect beneficial or desired results, including clinical results, and, as such, an effective amount or synonym thereof depends upon the context in which it is being applied. For example, in the context of IgG production or synthesis inhibition, it is an amount of the compound sufficient to achieve an inhibition of the increase of autoantibodies as determined by the respective IgG levels compared to the response obtained without administration of the compound. In the context of disease, therapeutically effective amounts of the antibody format are used to treat, modulate, attenuate, reverse, or affect a disease or condition that benefits from an inhibition of the autoimmune reactions, for example, acute or chronic inflammatory diseases associated with an auto-reactive B-cell disorder. An effective amount is intended to mean that amount of a compound that is sufficient to treat, prevent or inhibit such diseases or disorder. The amount of the antibody format that will correspond to such an amount will vary depending on various factors, such as the given drug or compound, the pharmaceutical formulation, the route of administration, the type of disease or disorder, the identity of the subject or host being treated, and the like, but can nevertheless be routinely determined by one skilled in the art.

A therapeutically effective amount of the antibody format such as provided to a human patient in need thereof may specifically be in the range of 0.5-500 mg, preferably 1-400 mg, even more preferred up to 300 mg, up to 200 mg, up to 100 mg or up to 10 mg, though higher doses may be indicated e.g. for treating acute disease conditions.

Moreover, a treatment or prevention regime of a subject with a therapeutically effective amount of the antibody format of the present invention may consist of a single administration, or alternatively comprise a series of applications. For example, the antibody format may be administered at least once a year, at least once a half-year or at least once a month. However, in another embodiment, the antibody format may be administered to the subject from about one time per week to about a daily administration for a given treatment. The length of the treatment period depends on a variety of factors, such as the severity of the disease, either acute or chronic disease, the age of the patient, the concentration and the activity of the antibody format. It will also be appreciated that the effective dosage used for the treatment or prophylaxis may increase or decrease over the course of a particular treatment or prophylaxis regime. Changes in dosage may result and become apparent by standard diagnostic assays known in the art. In some instances, chronic administration may be required.

Examplary formulations as used for parenteral administration include those suitable for subcutaneous, intramuscular or intravenous injection as, for example, a sterile solution or suspension.

The antibody format of the invention is typically used to reduce the symptoms of an autoimmune reaction, e.g. reducing the annual relapse rate in relapse-remitting MS (RRMS), e.g. to below 50%, preferably below 40% or below 30%. Other examples would be a rise in thrombocyte count by a factor of more than 2 in case of idiopathic thrombocytopenic purpura (ITP) or a rise in haemoglobin concentration of more than 2 mg/dl in case of an autoimmune hemolytic anemia.

In one embodiment, the antibody format according to the present invention is the only therapeutically active agent administered to a patient, e.g. as a disease modifying monotherapy.

Alternatively, the antibody format according the present invention is administered in combination with one or more other therapeutic agents, including but not limited to standard treatment, e.g. interferon-beta or steroids in case of MS or high dose immunoglobulins in case of ITP.

A combination therapy is particularly employing a standard regimen, e.g. as used for treating RRMS. This may include interferon-beta or steroids.

In a combination therapy, the antibody format may be administered as a mixture, or concomitantly with one or more other therapeutic regimens, e.g. either before, simultaneously or after concomitant therapy.

The biological properties of the antibody format according to the invention may be characterized ex vivo in cell, tissue, and whole organism experiments. As is known in the art, drugs are often tested in vivo in animals, including but not limited to mice, rats, rabbits, dogs, cats, pigs, and monkeys, in order to measure a drug's efficacy for treatment against a disease or disease model, or to measure a drug's pharmacokinetics, pharmacodynamics, toxicity, and other properties. The animals may be referred to as disease models. Therapeutics are often tested in mice, including but not limited to nude mice, SCID mice, xenograft mice, and transgenic mice (including knockins and knockouts). Such experimentation may provide meaningful data for determination of the potential of the antibody format to be used as a therapeutic with the appropriate half-life, effector function, apoptotic activity and IgG inhibitory activity. Any organism, preferably mammals, may be used for testing. For example because of their genetic similarity to humans, primates, monkeys can be suitable therapeutic models, and thus may be used to test the efficacy, toxicity, pharmacokinetics, pharmacodynamics, half-life, or other property of the antibody format according to the invention. Tests of the substances in humans are ultimately required for approval as drugs, and these experiments are contemplated herein. Thus the antibody format of the present invention may be tested in animal models or in humans to determine their therapeutic efficacy, toxicity, immunogenicity, pharmacokinetics, and/or other clinical properties.

The foregoing description will be more fully understood with reference to the following examples. Such examples are, however, merely representative of methods of practicing one or more embodiments of the present invention and should not be read as limiting the scope of invention.

EXAMPLES

Example 1A

Production of an Exemplary Antibody Format by Chemical Hybridization of Fab Fragments Bispecific (Fab')$_2$ antibodies as described above in FIG. 1A were prepared and as described in Jung et al. Eur. J. Immunol. 21:2431, 1991. Briefly, the CD20 antibody Rituximab was purchased from Roche Pharma AG (Germany), the CD95 antibody (Apo-1 antibody) was purified from hybridoma culture supernatants. The Apo-1 antibody can be purchased in purified form (BMS151) from eBioscience, San Diego, Calif. 92121 Antibodies were purified using Protein A affinity chromatography, and the myc antibody was obtained from supernatants of the hybridoma clone 9E10 (CRL-1729, ATCC Manassas, Va., USA). Both antibodies were digested by pepsin, modified and hybridized to obtain a bispecific Fab$_2$ fragment (bsFab2) as described in the paper mentioned above. Bispecific antibodies with CD40×CD95- and myc×CD95-specificity were produced accordingly. Parental antibodies directed to CD40 and the myc protein were purified from culture supernatants of hybridoma cells (ATCC Manassas, Va., USA).

In a general manner, the bispecific (Fab')$_2$ antibodies were prepared by oxidizing monovalent F(ab') fragments to obtain an (Fab')$_2$ fragment.

Alternatively, the bispecific (Fab')$_2$ antibodies may be produced by fusing two hybridoma cell lines to give quadroma cells, or by recombinant antibody technology.

Example 1B

Production of an Exemplary Antibody Format by Recombinant Engineering, Recombinant Bispecific Fab-Single Chain (Herein Also Called bsFabXsc or NA-C20)

Bispecific NA-C20 antibodies as described above in FIG. 1B were prepared and employing the sequences described in FIG. 9. The genetic construct encoding the antibody was stably transfected into Sp2/0 cells using standard techniques. The protein was purified from supernatants of transfected cells using affinity chromatography with kappa-select, purchased from GE-Healthcare, Life Sciences, Freiburg, Germany.

Example 2

Expression of CD95 on Human B-Cells Activated with 1 µg/mL PWM

Peripheral blood mononuclear cells (PBMC) of a normal healthy donor, isolated by density gradient centrifugation, were incubated with pokeweed mitogen (PWM, 1 µg/ml, Sigma Aldrich, Taufkirchen, Germany) for 6 days and washed. At the indicated time points cells were removed from the culture flasks and analyzed by flow cytometry. To this end cells were stained with a CD19 antibody or an isotype control antibody coupled to pacific blue, a CD95 antibody coupled to allophycocyanin (APC) and the 7-amino-actinomycin D (7-AAD) dye to clearly identify viable cells. Viable, CD19-positive cells were gated and analyzed. Antibodies were purchased from Biolegend, San Diego, Calif. 92121. Results are provided in FIG. 2. Bright profiles were obtained with an isotype control-dark profiles with the CD95 antibody.

Conclusion: While CD95 is not detectable on resting B cells its expression rises after 1 day of PWM stimulation, reaches its maximum at day three and remains high up to day 10 despite washing of the cells at day 6.

Example 3

Kinetic of IgG Production by PWM Activated B-Cells

Normal PBMC were stimulated with PWM (1 µg/ml). After various times aliquots of the culture supernatant were removed and analyzed by ELISA for human IgG content. Results are provided in FIG. 3. Stimulation of PBMC with PWM (full circle) induces production of human IgG. Antibody production becomes detectable at day 4 and rises continuously up to day 10. Measurement of antibody production of unstimulated PBMC (open circle) serves as control.

Conclusion: IgG production becomes detectable after 5 days of PWM stimulation and rises continuously up to day 10.

Example 4

Depletion of CD19+ B Cells and CD4/CD8+ T-Helper/Killer Cells from Unstimulated PBMC Unstimulated PBMC were incubated for 4 days with the antibodies indicated (1 µg/ml), washed and analyzed by flow cytometry using a CD19 antibody coupled to pacific blue, a CD4 antibody coupled to fluorescein isothiocyanate (FITC), a CD8 antibody coupled to APC and the viability dye 7-AAD (Biolegend, San Diego, Calif. 92121). NA-C20 is the recombinant bispecific antibody depicted in FIG. 1B. Results are provided in FIG. 4.

Conclusion: None of the indicated antibodies affects T cells or B cells in unstimulated PBMC cultures.

Example 5

Depletion of CD19+ B Cells and CD4/CD8+ T-Helper/Killer Cells from Stimulated PBMC PBMC were stimulated for 6 days with pokeweed mitogen (PWM, Sigma-Aldrich, 1 µg/ml), washed and incubated for 4 days with the antibodies indicated (1 µg/ml). Cells were analyzed by flow cytometry at day 10 as described in FIG. 4. Results are provided in FIG. 5. NA-C20 is the recombinant bispecific antibody in the bsFabXsc-format depicted in FIG. 1B.

Conclusion: The two bispecific CD20×CD95 antibodies induce depletion of B cells in PWM-stimulated PBMC. T cells are not affected. A chemically hybridized control antibody with Myc×CD95-specificity is ineffective.

Example 6

Suppression of Antibody Production In Vitro

Human peripheral blood mononuclear cells (PBMC) were isolated from heparinized blood by density gradient centrifugation, seeded at 1×10$^6$ cells/ml in 6 well plates and stimulated with the lectin pokeweed mitogen (PWM, 1 µg/ml, Sigma Aldrich). At day 6 cells were washed and the indicated antibodies were added. At day 10, the amount of human IgG in the supernatant was measured by ELISA. NA-C20 is the recombinant bispecific antibody in the bsFabXsc-format depicted in FIG. 1B. Results are provided in FIG. 6.

Conclusion: Both bispecific CD20×CD95 antibodies suppress IgG production by stimulated human PBMC. A chemically hybridized control antibody with Myc×CD95-specificities does not.

Example 7

Bispecific Antibody Mediated Suppression of PMW Induced IgG Synthesis In Vitro Human peripheral blood mononuclear cells (PBMC) of three different healthy donors (FIG. 7A-7C) were isolated from heparinized blood by density gradient centrifugation, seeded at 1×10$^6$ cells/ml in 6 well plates and stimulated with the lectin pokeweed mitogen (PWM, 1 µg/ml, Sigma Aldrich). At day 6, cells were washed and bispecific F(ab')$_2$ antibodies (i.e. the F(ab')$_2$ antibody format) were added. At day 10, the amount of human IgG in the supernatant was measured by ELISA. Bispecific antibodies tested were either specifically targeting CD20×CD95 (full circle) or CD40×CD95 (triangles). As a comparison, a bispecific antibody (i.e. the F(ab')$_2$ antibody format) with an unrelated target specificity directed to the intracellular myc-protein (myc×CD95) (open circle) was tested in parallel.

Conclusion:

Bispecific Fab$_2$ antibodies with CD20×CD95 or CD40×CD95-specificity suppress IgG production by activated human B cells in vitro, antibodies with Myc×CD95-specificity do not.

Example 8

Suppression of Tetanus Toxoid Specific IgG Production

PBMC of a donor, freshly vaccinated with tetanus toxoid, were stimulated with tetanus toxoid (25 ng/ml, Calbiochem, Merck Darmstadt, Germany) for 4 days, washed and incubated with the indicated antibodies (1 µg/ml) for 8 days. At day 12 the amount of specific anti-tetanus antibodies was determined by ELISA. NA-C20 is the recombinant bispecific CD20×CD95 antibody in the bsFabXsc-format depicted in FIG. 1B. Results are provided in FIG. 8.

Conclusion: The recombinant bispecific CD20×CD95 antibody NA-C20 and the monospecific anti-CD20 antibody Rituxan suppress the production of specific anti-tetanus toxoid antibodies in vitro. Corresponding mono- and bispecific antibodies with unrelated target specificities directed either to the EGF-receptor (Erbitux) or to CD95 and the melanoma associated proteoglycan (NA-CMeI), respectively, are ineffective. NA-CMeI is a recombinant bispecific antibody of the same format as NA-C20.

The invention claimed is:

1. A method for the treatment of a B-cell-mediated autoimmune disease comprising administering a therapeutically effective amount of a bispecific antibody devoid of an active Fc moiety, wherein the antibody comprises a monovalent binding site for a B-cell CD95 death receptor and at least one binding site for a cell surface antigen expressed on B-cells to a subject in need thereof, wherein the cell surface antigen is selected from the group consisting of CD19, CD20 and CD40.

2. The method of claim 1, wherein the B-cell mediated autoimmune disease is caused by an aberrant, excessive or undesired immune response.

3. The method of claim 1, wherein the B-cell mediated autoimmune disease is selected from the group consisting of systemic lupus erythematosus, scleroderma, rheumatoid arthritis, juvenile idiopathic arthritis, graft versus host disease, dermatomyositis, type I diabetes mellitus, Hashimoto's thyroiditis, Graves's disease, Addison's disease, celiac disease, Crohn's Disease, pernicious anaemia Pemphigus vulgaris, Vitiligo, autoimmune haemolytic anaemia, idiopathic thrombocytopenic purpura, giant cell arteritis, Myasthenia gravis, multiple sclerosis (MS), preferably relapsing-remitting MS (RRMS), glomerulonephritis, Goodpasture's syndrome, bullous pemphigoid, colitis ulcerosa, Guillain-Barré syndrome, chronic inflammatory demyelinating polyneuropathy, Anti-phospholipid syndrome, narcolepsy, sarcoidosis, and Wegener's granulomatosis.

4. The method of claim 1, wherein the antibody is a recombinant molecule comprising at least 2 antibody domains having at least 3, 4, 5, 6, 7 or 8 antibody domains, and optionally a hinge region, wherein the format comprises at least one of a VH/VL binding site and/or scFV binding site, and optionally at least one of an antibody constant domain, specifically a CH1, CL, CH2 or CH3 domain.

5. The method of claim 4, wherein the antibody domains are of human origin or humanized antibody domains of mammalian origin other than human.

6. The method of claim 5, wherein the antibody domains are humanized and of murine or camelid origin.

7. The method of claim 1, wherein the antibody comprises at least two binding sites formed by complementary determining regions (CDR).

8. The method of claim 7, wherein the CDRs are derived from at least one or two VH domains and/or at least one or two VH/VL domain pairs.

9. The method of claim 1, wherein the antibody comprises at least one of a VH/VL binding site and/or scFv binding site, and optionally at least one of a CH1, CL, CH2 or CH3 domain.

10. The method of claim 1, wherein the antibody is lacking an Fc moiety or comprises an Fc moiety engineered to inactivate or reduce its Fc effector function.

11. The method of claim 10, wherein the Fc moiety comprises one or more mutations.

12. The method of claim 1, wherein the antibody is selected from the group consisting of scFv, a combination of a Fab fragment with one or more antibody variable domains, F(ab')$_2$, and combinations thereof.

13. The method of claim 12, wherein the format further comprises at least one antibody constant domain as a linker.

14. The method of claim 1, wherein the antibody comprises
a Fab fragment comprising a first binding site for a first antigen;
an scFv fragment comprising a second binding site for a second antigen; and
a CH2 domain, wherein the Fab fragment and the scFv fragment are linked via the CH2 domain, wherein
a) the first antigen is CD95 and the second antigen is selected from CD19, CD20 and CD40; or
b) the first antigen is selected from CD19, CD20 and CD40, and the second antigen is CD95.

15. The method of claim 14, wherein the binding site that binds CD20 comprises six complementarity determining regions of antibody variable domains (CDR1 to CDR6), wherein
A)
i) CDR1 comprises the amino acid sequence RASSSVSYM (SEQ ID NO:12);
ii) CDR2 comprises the amino acid sequence APSNLAS (SEQ ID NO:13);
iii) CDR3 comprises the amino acid sequence QQWSFNPPT (SEQ ID NO:14);
iv) CDR4 comprises the amino acid sequence SYNMH (SEQ ID NO:16);
v) CDR5 comprises the amino acid sequence AIYPGNGDTSYNQKFKG (SEQ ID NO:17); and
vi) CDR6 comprises the amino acid sequence VVYYSNSYWYFDV (SEQ ID NO:18).

16. The method of claim 14, wherein the binding site that binds CD95 comprises six complementarity determining regions of variable antibody domains (CDR1 to CDR6), wherein
A)
i) CDR1 comprises the amino acid sequence RASESVEYYGTSLMQ (SEQ ID NO:2);
ii) CDR2 comprises the amino acid sequence VASNVES (SEQ ID NO:3);
iii) CDR3 comprises the amino acid sequence QQSTKVPWT (SEQ ID NO:4);
iv) CDR4 comprises the amino acid sequence TNAMN (SEQ ID NO:6);
v) CDR5 comprises the amino acid sequence RIRSKSNNYATYYAESVKD (SEQ ID NO:7); and
vi) CDR6 comprises the amino acid sequence DGYY (SEQ ID NO:8).

17. The method of claim 14, wherein the first or second antigen is CD20.

18. The method of claim 1, wherein the antibody comprises a VL domain comprising the amino acid sequence of SEQ ID NO:11 and/or a VH domain comprising the amino acid sequence of SEQ ID NO:15, or functionally active variants thereof.

19. The method of claim 18, wherein the variant is a humanized variant comprising a VL domain comprising the amino acid sequence of SEQ ID NO:19 and/or a VH domain comprising the amino acid sequence of SEQ ID NO:20, or a functionally active variant thereof.

20. The method of claim 1, wherein the antibody comprises a VL domain comprising the amino acid sequence of SEQ ID NO:1 and/or a VH domain comprising the amino acid sequence of SEQ ID NO:5, or functionally active variants thereof.

21. The method of claim 20, wherein the variant is a humanized variant comprising a VL domain comprising the amino acid sequence of SEQ ID NO:9 and/or a VH domain comprising the amino acid sequence of SEQ ID NO:10.

22. The method of claim 1, wherein the antibody comprises a light chain sequence of SEQ ID NO:21 and a heavy chain sequence of SEQ ID NO:22, or functionally active variants thereof.

23. The method of claim 22, wherein the variant is a humanized variant comprising a VL domain comprising the amino acid sequence of SEQ ID NO:24 and/or a VH domain comprising the amino acid sequence of SEQ ID NO:25.

24. The method of claim 1, wherein the antibody comprises murine, chimeric and/or humanized sequences.

25. The method of claim 1, wherein the antibody binds CD20 with a Kd<$10^{-8}$ M and/or binds CD95 with a Kd<$10^{-8}$ M.

26. The method of claim 1, further comprising another treatment of a B-cell mediated autoimmune disease.

27. The method of claim 26, wherein the other treatment is a cytokine treatment or treatment with another antibody format or agent.

28. The method of claim 1, wherein the cell surface antigen is CD20.

29. A method for treating auto-reactive B-cells, comprising contacting said cells with a composition comprising a bispecific antibody devoid of an active Fc moiety, wherein the antibody comprises a monovalent binding site for a B-cell CD95 death receptor and at least one binding site for a cell surface antigen expressed on B-cells to a subject in need thereof, wherein the cell surface antigen is selected from the group consisting of CD19, CD20 and CD40.

30. The method of claim 29, wherein the death receptor and the cell surface antigen being expressed by said cells are targeted by the bispecific antibody, whereby the IgG production by said cells is inhibited.

* * * * *

SEQUENCE LISTING

```
<160> NUMBER OF SEQ ID NOS: 25

<210> SEQ ID NO 1
<211> LENGTH: 112
<212> TYPE: PRT
<213> ORGANISM: artificial
<220> FEATURE:
<223> OTHER INFORMATION: VL Sequence

<400> SEQUENCE: 1

Asp Ile Val Leu Thr Gln Ser Pro Ala Ser Leu Ala Val Ser Leu Gly
1               5                   10                  15
```

```
Gln Arg Ala Thr Ile Ser Cys Arg Ala Ser Glu Ser Val Glu Tyr Tyr
                20                  25                  30

Gly Thr Ser Leu Met Gln Trp Tyr Gln Gln Lys Pro Gly Gln Pro Pro
            35                  40                  45

Lys Leu Leu Ile Tyr Val Ala Ser Asn Val Glu Ser Gly Val Pro Ala
50                      55                  60

Arg Phe Ser Gly Ser Gly Ser Gly Thr Asp Phe Ser Leu Asn Ile His
65                  70                  75                  80

Pro Val Glu Glu Asp Asp Ile Ala Met Tyr Phe Cys Gln Gln Ser Thr
                85                  90                  95

Lys Val Pro Trp Thr Phe Gly Gly Thr Lys Leu Glu Ile Lys Arg
            100                 105                 110
```

<210> SEQ ID NO 2
<211> LENGTH: 15
<212> TYPE: PRT
<213> ORGANISM: artificial
<220> FEATURE:
<223> OTHER INFORMATION: CDR Sequence

<400> SEQUENCE: 2

```
Arg Ala Ser Glu Ser Val Glu Tyr Tyr Gly Thr Ser Leu Met Gln
1               5                   10                  15
```

<210> SEQ ID NO 3
<211> LENGTH: 7
<212> TYPE: PRT
<213> ORGANISM: artificial
<220> FEATURE:
<223> OTHER INFORMATION: CDR Sequence

<400> SEQUENCE: 3

```
Val Ala Ser Asn Val Glu Ser
1               5
```

<210> SEQ ID NO 4
<211> LENGTH: 9
<212> TYPE: PRT
<213> ORGANISM: artificial
<220> FEATURE:
<223> OTHER INFORMATION: CDR Sequence

<400> SEQUENCE: 4

```
Gln Gln Ser Thr Lys Val Pro Trp Thr
1               5
```

<210> SEQ ID NO 5
<211> LENGTH: 115
<212> TYPE: PRT
<213> ORGANISM: artificial
<220> FEATURE:
<223> OTHER INFORMATION: VH Sequence

<400> SEQUENCE: 5

```
Glu Val Gln Leu Val Glu Thr Gly Gly Gly Leu Val Gln Pro Lys Gly
1               5                   10                  15

Ser Leu Lys Leu Ser Cys Ala Ala Ser Gly Phe Thr Phe Asn Thr Asn
                20                  25                  30

Ala Met Asn Trp Val Arg Gln Ala Pro Gly Lys Gly Leu Glu Trp Val
            35                  40                  45

Ala Arg Ile Arg Ser Lys Ser Asn Asn Tyr Ala Thr Tyr Tyr Ala Glu
50                  55                  60
```

```
Ser Val Lys Asp Arg Phe Thr Ile Ser Arg Asp Asp Ser Gln Ser Met
 65                  70                  75                  80

Leu Tyr Leu Gln Met Asn Asn Leu Lys Ala Glu Asp Thr Ala Met Tyr
                 85                  90                  95

Tyr Cys Val Thr Asp Gly Tyr Tyr Trp Gly Gln Gly Thr Thr Leu Thr
            100                 105                 110

Val Ser Ser
        115

<210> SEQ ID NO 6
<211> LENGTH: 5
<212> TYPE: PRT
<213> ORGANISM: artificial
<220> FEATURE:
<223> OTHER INFORMATION: CDR Sequence

<400> SEQUENCE: 6

Thr Asn Ala Met Asn
1               5

<210> SEQ ID NO 7
<211> LENGTH: 19
<212> TYPE: PRT
<213> ORGANISM: artificial
<220> FEATURE:
<223> OTHER INFORMATION: CDR Sequence

<400> SEQUENCE: 7

Arg Ile Arg Ser Lys Ser Asn Asn Tyr Ala Thr Tyr Tyr Ala Glu Ser
1               5                   10                  15

Val Lys Asp

<210> SEQ ID NO 8
<211> LENGTH: 4
<212> TYPE: PRT
<213> ORGANISM: artificial
<220> FEATURE:
<223> OTHER INFORMATION: CDR Sequence

<400> SEQUENCE: 8

Asp Gly Tyr Tyr
1

<210> SEQ ID NO 9
<211> LENGTH: 111
<212> TYPE: PRT
<213> ORGANISM: artificial
<220> FEATURE:
<223> OTHER INFORMATION: VL Sequence

<400> SEQUENCE: 9

Asp Ile Val Met Thr Gln Ser Pro Asp Ser Leu Ala Val Ser Leu Gly
1               5                   10                  15

Glu Arg Ala Thr Ile Ser Cys Arg Ala Ser Gln Ser Val Glu Tyr Tyr
                20                  25                  30

Gly Thr Ser Leu Met Gln Trp Tyr Gln Gln Lys Pro Gly Gln Pro Pro
            35                  40                  45

Lys Leu Leu Ile Tyr Val Ala Ser Asn Val Glu Ser Gly Val Pro Asp
        50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Phe Cys Gln Gln Ser Thr
```

```
                        85                  90                  95

Lys Val Pro Trp Thr Phe Gly Gln Gly Thr Lys Leu Glu Ile Lys
            100                 105                 110

<210> SEQ ID NO 10
<211> LENGTH: 115
<212> TYPE: PRT
<213> ORGANISM: artificial
<220> FEATURE:
<223> OTHER INFORMATION: VH Sequence

<400> SEQUENCE: 10

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Asn Thr Asn
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Glu
    50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Val Thr Asp Gly Tyr Tyr Trp Gly Gln Gly Thr Thr Leu Thr
            100                 105                 110

Val Ser Ser
        115

<210> SEQ ID NO 11
<211> LENGTH: 106
<212> TYPE: PRT
<213> ORGANISM: artificial
<220> FEATURE:
<223> OTHER INFORMATION: VL Sequence

<400> SEQUENCE: 11

Asp Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
            20                  25                  30

His Trp Tyr Gln Gln Lys Pro Gly Ser Ser Pro Lys Pro Trp Ile Tyr
        35                  40                  45

Ala Pro Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Phe Asn Pro Pro Thr
                85                  90                  95

Phe Gly Ala Gly Thr Lys Leu Glu Leu Lys
            100                 105

<210> SEQ ID NO 12
<211> LENGTH: 9
<212> TYPE: PRT
<213> ORGANISM: artificial
<220> FEATURE:
<223> OTHER INFORMATION: CDR Sequence

<400> SEQUENCE: 12
```

```
Arg Ala Ser Ser Ser Val Ser Tyr Met
1               5

<210> SEQ ID NO 13
<211> LENGTH: 7
<212> TYPE: PRT
<213> ORGANISM: artificial
<220> FEATURE:
<223> OTHER INFORMATION: CDR Sequence

<400> SEQUENCE: 13

Ala Pro Ser Asn Leu Ala Ser
1               5

<210> SEQ ID NO 14
<211> LENGTH: 9
<212> TYPE: PRT
<213> ORGANISM: artificial
<220> FEATURE:
<223> OTHER INFORMATION: CDR Sequence

<400> SEQUENCE: 14

Gln Gln Trp Ser Phe Asn Pro Pro Thr
1               5

<210> SEQ ID NO 15
<211> LENGTH: 122
<212> TYPE: PRT
<213> ORGANISM: artificial
<220> FEATURE:
<223> OTHER INFORMATION: VH Sequence

<400> SEQUENCE: 15

Gln Ala Tyr Leu Gln Gln Ser Gly Ala Glu Leu Val Arg Pro Gly Ala
1               5                   10                  15

Ser Val Lys Met Ser Cys Lys Ala Ser Gly Tyr Thr Phe Thr Ser Tyr
                20                  25                  30

Asn Met His Trp Val Lys Gln Thr Pro Arg Gln Gly Leu Glu Trp Ile
            35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Val Val Tyr Tyr Ser Asn Ser Tyr Trp Tyr Phe Asp Val Trp
            100                 105                 110

Gly Thr Gly Thr Thr Val Thr Val Ser Ser
        115                 120

<210> SEQ ID NO 16
<211> LENGTH: 5
<212> TYPE: PRT
<213> ORGANISM: artificial
<220> FEATURE:
<223> OTHER INFORMATION: CDR Sequence

<400> SEQUENCE: 16

Ser Tyr Asn Met His
1               5

<210> SEQ ID NO 17
```

```
<211> LENGTH: 17
<212> TYPE: PRT
<213> ORGANISM: artificial
<220> FEATURE:
<223> OTHER INFORMATION: CDR Sequence

<400> SEQUENCE: 17

Ala Ile Tyr Pro Gly Asn Gly Asp Thr Ser Tyr Asn Gln Lys Phe Lys
1               5                   10                  15

Gly

<210> SEQ ID NO 18
<211> LENGTH: 13
<212> TYPE: PRT
<213> ORGANISM: artificial
<220> FEATURE:
<223> OTHER INFORMATION: CDR Sequence

<400> SEQUENCE: 18

Val Val Tyr Tyr Ser Asn Ser Tyr Trp Tyr Phe Asp Val
1               5                   10

<210> SEQ ID NO 19
<211> LENGTH: 106
<212> TYPE: PRT
<213> ORGANISM: artificial
<220> FEATURE:
<223> OTHER INFORMATION: VL Sequence

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Met
            20                  25                  30

His Trp Tyr Gln Gln Lys Pro Gly Lys Ala Pro Lys Pro Leu Ile Tyr
        35                  40                  45

Ala Pro Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Phe Asn Pro Pro Thr
                85                  90                  95

Phe Gly Gln Gly Thr Lys Leu Glu Ile Lys
            100                 105

<210> SEQ ID NO 20
<211> LENGTH: 122
<212> TYPE: PRT
<213> ORGANISM: artificial
<220> FEATURE:
<223> OTHER INFORMATION: VH Sequence

<400> SEQUENCE: 20

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asn Met His Trp Val Arg Gln Ala Pro Gly Gln Gly Leu Glu Trp Ile
        35                  40                  45

Gly Ala Ile Tyr Pro Gly Asn Gly Asp Thr Ser Tyr Asn Gln Lys Phe
    50                  55                  60
```

```
Lys Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
             85                  90                  95

Ala Arg Val Val Tyr Tyr Ser Asn Ser Tyr Trp Tyr Phe Asp Val Trp
            100                 105                 110

Gly Gln Gly Thr Leu Val Thr Val Ser Ser
        115                 120
```

<210> SEQ ID NO 21
<211> LENGTH: 218
<212> TYPE: PRT
<213> ORGANISM: artificial
<220> FEATURE:
<223> OTHER INFORMATION: LC Sequence

<400> SEQUENCE: 21

```
Asp Ile Val Leu Thr Gln Ser Pro Ala Ser Leu Ala Val Ser Leu Gly
 1               5                  10                  15

Gln Arg Ala Thr Ile Ser Cys Arg Ala Ser Glu Ser Val Glu Tyr Tyr
             20                  25                  30

Gly Thr Ser Leu Met Gln Trp Tyr Gln Gln Lys Pro Gly Gln Pro Pro
         35                  40                  45

Lys Leu Leu Ile Tyr Val Ala Ser Asn Val Glu Ser Gly Val Pro Ala
 50                  55                  60

Arg Phe Ser Gly Ser Gly Ser Gly Thr Asp Phe Ser Leu Asn Ile His
 65                  70                  75                  80

Pro Val Glu Glu Asp Asp Ile Ala Met Tyr Phe Cys Gln Gln Ser Thr
             85                  90                  95

Lys Val Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
210                 215
```

<210> SEQ ID NO 22
<211> LENGTH: 585
<212> TYPE: PRT
<213> ORGANISM: artificial
<220> FEATURE:
<223> OTHER INFORMATION: HC Sequence

<400> SEQUENCE: 22

```
Glu Val Gln Leu Val Glu Thr Gly Gly Gly Leu Val Gln Pro Lys Gly
 1               5                  10                  15

Ser Leu Lys Leu Ser Cys Ala Ala Ser Gly Phe Thr Phe Asn Thr Asn
             20                  25                  30
```

```
Ala Met Asn Trp Val Arg Gln Ala Pro Gly Lys Gly Leu Glu Trp Val
        35                  40                  45
Ala Arg Ile Arg Ser Lys Ser Asn Asn Tyr Ala Thr Tyr Tyr Ala Glu
 50                  55                  60
Ser Val Lys Asp Arg Phe Thr Ile Ser Arg Asp Asp Ser Gln Ser Met
 65                  70                  75                  80
Leu Tyr Leu Gln Met Asn Asn Leu Lys Ala Glu Asp Thr Ala Met Tyr
                 85                  90                  95
Tyr Cys Val Thr Asp Gly Tyr Tyr Trp Gly Gln Gly Thr Thr Leu Thr
                100                 105                 110
Val Ser Ser Ala Ser Thr Lys Gly Pro Ser Val Phe Pro Leu Ala Pro
            115                 120                 125
Ser Ser Lys Ser Thr Ser Gly Gly Thr Ala Ala Leu Gly Cys Leu Val
        130                 135                 140
Lys Asp Tyr Phe Pro Glu Pro Val Thr Val Ser Trp Asn Ser Gly Ala
145                 150                 155                 160
Leu Thr Ser Gly Val His Thr Phe Pro Ala Val Leu Gln Ser Ser Gly
                165                 170                 175
Leu Tyr Ser Leu Ser Ser Val Val Thr Val Pro Ser Ser Ser Leu Gly
            180                 185                 190
Thr Gln Thr Tyr Ile Cys Asn Val Asn His Lys Pro Ser Asn Thr Lys
        195                 200                 205
Val Asp Lys Lys Val Glu Pro Lys Ser Cys Asp Lys Thr His Thr Ser
    210                 215                 220
Pro Pro Ser Pro Ala Pro Val Ala Gly Pro Ser Val Phe Leu Phe
225                 230                 235                 240
Pro Pro Lys Pro Lys Asp Thr Leu Met Ile Ser Arg Thr Pro Glu Val
                245                 250                 255
Thr Cys Val Val Val Gly Val Ser His Glu Asp Pro Glu Val Lys Phe
            260                 265                 270
Asn Trp Tyr Val Asp Gly Val Glu Val His Asn Ala Lys Thr Lys Pro
        275                 280                 285
Arg Glu Glu Gln Tyr Gln Ser Thr Tyr Arg Val Val Ser Val Leu Thr
    290                 295                 300
Val Leu His Gln Asp Trp Leu Asn Gly Lys Glu Tyr Lys Cys Lys Val
305                 310                 315                 320
Ser Asn Lys Gln Leu Pro Ser Pro Ile Glu Lys Thr Ile Ser Lys Ala
                325                 330                 335
Lys Gly Gln Pro Ser Gly Gln Ala Tyr Leu Gln Gln Ser Gly Ala Glu
            340                 345                 350
Leu Val Arg Pro Gly Ala Ser Val Lys Met Ser Cys Lys Ala Ser Gly
        355                 360                 365
Tyr Thr Phe Thr Ser Tyr Asn Met His Trp Val Lys Gln Thr Pro Arg
    370                 375                 380
Gln Gly Leu Glu Trp Ile Gly Ala Ile Tyr Pro Gly Asn Gly Asp Thr
385                 390                 395                 400
Ser Tyr Asn Gln Lys Phe Lys Gly Lys Ala Thr Leu Thr Val Asp Lys
                405                 410                 415
Ser Ser Ser Thr Ala Tyr Met Gln Leu Ser Ser Leu Thr Ser Glu Asp
            420                 425                 430
Ser Ala Val Tyr Phe Cys Ala Arg Val Val Tyr Tyr Ser Asn Ser Tyr
        435                 440                 445
```

```
Trp Tyr Phe Asp Val Trp Gly Thr Gly Thr Thr Val Thr Val Ser Ser
        450                 455                 460

Gly Gly Gly Gly Ser Gly Gly Gly Ser Gly Gly Gly Gly Ser Asp
465                 470                 475                 480

Ile Val Leu Ser Gln Ser Pro Ala Ile Leu Ser Ala Ser Pro Gly Glu
                485                 490                 495

Lys Val Thr Met Thr Cys Arg Ala Ser Ser Ser Val Ser Tyr Met His
                500                 505                 510

Trp Tyr Gln Gln Lys Pro Gly Ser Ser Pro Lys Pro Trp Ile Tyr Ala
                515                 520                 525

Pro Ser Asn Leu Ala Ser Gly Val Pro Ala Arg Phe Ser Gly Ser Gly
530                 535                 540

Ser Gly Thr Ser Tyr Ser Leu Thr Ile Ser Arg Val Glu Ala Glu Asp
545                 550                 555                 560

Ala Ala Thr Tyr Tyr Cys Gln Gln Trp Ser Phe Asn Pro Pro Thr Phe
                565                 570                 575

Gly Ala Gly Thr Lys Leu Glu Leu Lys
                580                 585

<210> SEQ ID NO 23
<211> LENGTH: 15
<212> TYPE: PRT
<213> ORGANISM: artificial
<220> FEATURE:
<223> OTHER INFORMATION: Linker

<400> SEQUENCE: 23

Gly Gly Gly Gly Ser Gly Gly Gly Ser Gly Gly Gly Gly Ser
1               5                   10                  15

<210> SEQ ID NO 24
<211> LENGTH: 218
<212> TYPE: PRT
<213> ORGANISM: artificial
<220> FEATURE:
<223> OTHER INFORMATION: LC Sequence

<400> SEQUENCE: 24

Asp Ile Val Met Thr Gln Ser Pro Asp Ser Leu Ala Val Ser Leu Gly
1               5                   10                  15

Glu Arg Ala Thr Ile Ser Cys Arg Ala Ser Glu Ser Val Glu Tyr Tyr
                20                  25                  30

Gly Thr Ser Leu Met Gln Trp Tyr Gln Gln Lys Pro Gly Gln Pro Pro
            35                  40                  45

Lys Leu Leu Ile Tyr Val Ala Ser Asn Val Glu Ser Gly Val Pro Asp
50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Phe Cys Gln Gln Ser Thr
                85                  90                  95

Lys Val Pro Trp Thr Phe Gly Gln Gly Thr Lys Leu Glu Ile Lys Arg
                100                 105                 110

Thr Val Ala Ala Pro Ser Val Phe Ile Phe Pro Pro Ser Asp Glu Gln
                115                 120                 125

Leu Lys Ser Gly Thr Ala Ser Val Val Cys Leu Leu Asn Asn Phe Tyr
            130                 135                 140

Pro Arg Glu Ala Lys Val Gln Trp Lys Val Asp Asn Ala Leu Gln Ser
145                 150                 155                 160
```

Gly Asn Ser Gln Glu Ser Val Thr Glu Gln Asp Ser Lys Asp Ser Thr
            165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
            210                 215

<210> SEQ ID NO 25
<211> LENGTH: 585
<212> TYPE: PRT
<213> ORGANISM: artificial
<220> FEATURE:
<223> OTHER INFORMATION: HC Sequence

<400> SEQUENCE: 25

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Asn Thr Asn
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Glu
    50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Val Thr Asp Gly Tyr Tyr Trp Gly Gln Gly Thr Thr Leu Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Ser
    210                 215                 220

Pro Pro Ser Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Gly Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Gln Ser Thr Tyr Arg Val Val Ser Val Leu Thr
    290                 295                 300

```
Val Leu His Gln Asp Trp Leu Asn Gly Lys Glu Tyr Lys Cys Lys Val
305                 310                 315                 320
Ser Asn Lys Gln Leu Pro Ser Pro Ile Glu Lys Thr Ile Ser Lys Ala
                325                 330                 335
Lys Gly Gln Pro Ser Gly Gln Val Gln Leu Val Gln Ser Gly Ala Glu
            340                 345                 350
Val Lys Lys Pro Gly Ala Ser Val Lys Val Ser Cys Lys Ala Ser Gly
        355                 360                 365
Tyr Thr Phe Thr Ser Tyr Asn Met His Trp Val Arg Gln Ala Pro Gly
    370                 375                 380
Gln Gly Leu Glu Trp Ile Gly Ala Ile Tyr Pro Gly Asn Gly Asp Thr
385                 390                 395                 400
Ser Tyr Asn Gln Lys Phe Lys Gly Arg Val Thr Ile Thr Arg Asp Thr
                405                 410                 415
Ser Ala Ser Thr Ala Tyr Met Glu Leu Ser Ser Leu Arg Ser Glu Asp
            420                 425                 430
Thr Ala Val Tyr Tyr Cys Ala Arg Val Val Tyr Tyr Ser Asn Ser Tyr
        435                 440                 445
Trp Tyr Phe Asp Val Trp Gly Gln Gly Thr Leu Val Thr Val Ser Ser
    450                 455                 460
Gly Gly Gly Gly Ser Gly Gly Gly Gly Ser Gly Gly Gly Gly Ser Asp
465                 470                 475                 480
Ile Gln Met Thr Gln Ser Pro Ser Ser Leu Ser Ala Ser Val Gly Asp
                485                 490                 495
Arg Val Thr Ile Thr Cys Arg Ala Ser Ser Ser Val Ser Tyr Met His
            500                 505                 510
Trp Tyr Gln Gln Lys Pro Gly Lys Ala Pro Lys Pro Leu Ile Tyr Ala
        515                 520                 525
Pro Ser Asn Leu Ala Ser Gly Val Pro Ser Arg Phe Ser Gly Ser Gly
    530                 535                 540
Ser Gly Thr Asp Phe Thr Leu Thr Ile Ser Ser Leu Gln Pro Glu Asp
545                 550                 555                 560
Phe Ala Thr Tyr Tyr Cys Gln Gln Trp Ser Phe Asn Pro Pro Thr Phe
                565                 570                 575
Gly Gln Gly Thr Lys Leu Glu Ile Lys
            580                 585
```